US012704210B2

(12) United States Patent
Wine

(10) Patent No.: US 12,704,210 B2
(45) Date of Patent: Aug. 11, 2026

(54) CONNECTOR COUPLING ASSEMBLY

(71) Applicant: CareFusion 303, Inc., San Diego, CA (US)

(72) Inventor: Jason Andrew Wine, Brea, CA (US)

(73) Assignee: CAREFUSION 303, INC., San Diego, CA (US)

( * ) Notice: Subject to any disclaimer, the term of this patent is extended or adjusted under 35 U.S.C. 154(b) by 100 days.

(21) Appl. No.: 18/508,664

(22) Filed: Nov. 14, 2023

(65) Prior Publication Data

US 2024/0167602 A1 May 23, 2024

Related U.S. Application Data

(60) Provisional application No. 63/426,430, filed on Nov. 18, 2022.

(51) Int. Cl.
*F16L 37/084* (2006.01)
*A61M 39/10* (2006.01)
(Continued)

(52) U.S. Cl.
CPC ....... *F16L 37/0841* (2013.01); *F16L 37/0985* (2013.01); *F16L 37/30* (2013.01);
(Continued)

(58) Field of Classification Search
CPC ....... F16L 19/0206; F16L 37/32; F16L 37/33; F16L 37/34; F16L 37/35; F16L 19/06;
(Continued)

(56) References Cited

U.S. PATENT DOCUMENTS

| | | | | | |
|---|---|---|---|---|---|
| 4,084,614 | A * | 4/1978 | Ekman | F16L 37/33 137/614.04 |
| 4,700,743 | A * | 10/1987 | L'Henaff | F16L 37/35 137/614.04 |

(Continued)

FOREIGN PATENT DOCUMENTS

| | | |
|---|---|---|
| EP | 1678070 A2 | 7/2006 |
| EP | 1517723 B1 | 1/2007 |

(Continued)

OTHER PUBLICATIONS

International Search Report and Written Opinion for Application No. PCT/US2023/080090, dated Mar. 15, 2024, 11 pages.

(Continued)

*Primary Examiner* — Kenneth Rinehart
*Assistant Examiner* — Jonathan J Waddy
(74) *Attorney, Agent, or Firm* — MASCHOFF BRENNAN

(57) ABSTRACT

A coupler including a first connector having a first end, a second end opposite the first end, and a first valve disposed between the first end and the second end, a second connector having a mating portion, a connecting portion opposite the mating portion, and a second valve disposed at least partially within the mating portion, and a collar having a body detachably coupled to the mating portion of the second connector and a releasing portion disposed opposite the body, the releasing portion configured to receive at least a portion of the first connector to detachably couple the first connector to the collar and the second connector such that the first end of the first connector is disposed within the second connector. The first connector is configured to decouple from the collar and the second connector and is prevented from re-coupling to the collar once decoupled.

19 Claims, 22 Drawing Sheets

(51) Int. Cl.
*A61M 39/26* (2006.01)
*F16L 37/098* (2006.01)
*F16L 37/30* (2006.01)

(52) U.S. Cl.
CPC ............... *A61M 2039/1027* (2013.01); *A61M 2039/267* (2013.01)

(58) Field of Classification Search
CPC . F16L 37/0847; F16L 37/088; F16L 37/0885; F16L 37/091; F16L 37/098; F16L 37/0985; F16L 37/12; F16L 37/1225; F16L 37/133; F16L 37/138; F16L 37/30; F16L 37/38; A61M 39/10; A61M 39/1011; A61M 39/105; A61M 39/1055; A61M 39/26; A61M 2039/1016; A61M 2039/1027; A61M 2039/1038; A61M 2039/1061; A61M 2039/1072; A61M 2039/1077; A61M 2039/1083; A61M 2039/1088; A61M 2039/267
USPC ....................................................... 251/149.6
See application file for complete search history.

(56) References Cited

U.S. PATENT DOCUMENTS 5,249,830 A * 10/1993 Calmettes ........... F16L 37/0985 285/29
5,255,714 A * 10/1993 Mullins ................... F16L 37/33 285/91
5,482,083 A * 1/1996 Jenski ..................... F16L 37/35 285/307
5,713,856 A 2/1998 Eggers et al.
5,740,835 A * 4/1998 Murphy ................ F16L 37/138 251/149.6
6,283,443 B1 * 9/2001 Taneya .................... F16L 37/23 251/149.6
6,874,522 B2 4/2005 Anderson et al.
7,004,934 B2 2/2006 Vaillancourt
7,040,598 B2 5/2006 Raybuck
7,153,296 B2 12/2006 Mitchell
7,350,764 B2 4/2008 Raybuck
7,396,051 B2 7/2008 Baldwin et al.
7,763,013 B2 7/2010 Baldwin et al.
7,766,394 B2 8/2010 Sage et al.
7,794,675 B2 9/2010 Lynn
7,803,139 B2 9/2010 Fangrow, Jr.
7,803,140 B2 9/2010 Fangrow, Jr.
7,815,614 B2 10/2010 Fangrow, Jr.
7,918,243 B2 4/2011 Diodati et al.
7,998,134 B2 8/2011 Fangrow et al.
8,123,738 B2 2/2012 Vaillancourt
8,142,418 B2 3/2012 Mcmichael et al.
8,211,069 B2 7/2012 Fangrow, Jr.
8,262,628 B2 9/2012 Fangrow, Jr.
8,361,408 B2 1/2013 Lynn
8,480,968 B2 7/2013 Lynn
8,777,908 B2 7/2014 Fangrow, Jr.
8,777,909 B2 7/2014 Fangrow, Jr.
8,795,256 B1 8/2014 Smith
8,888,758 B2 11/2014 Mansour
8,899,267 B2 12/2014 Diodati et al.
8,910,919 B2 12/2014 Bonnal et al.
8,974,425 B2 3/2015 Tachizaki et al.
8,974,437 B2 3/2015 Williams et al.
9,114,242 B2 8/2015 Fangrow et al.
9,126,028 B2 9/2015 Fangrow et al.
9,126,029 B2 9/2015 Fangrow et al.
9,192,753 B2 11/2015 Lopez et al.
9,234,616 B2 1/2016 Carrez et al.
9,358,379 B2 6/2016 Fangrow, Jr.
9,433,769 B2 9/2016 Bayly
9,468,749 B2 10/2016 Mansour et al.
9,492,649 B2 11/2016 Carrez et al.
9,636,492 B2 5/2017 Fangrow, Jr.
9,724,504 B2 8/2017 Fangrow, Jr. et al.
9,724,505 B2 8/2017 Williams et al.
9,861,805 B2 1/2018 Dennis et al.
9,933,094 B2 4/2018 Fangrow
9,974,939 B2 5/2018 Fangrow, Jr.
9,974,940 B2 5/2018 Fangrow, Jr.
10,029,086 B2 7/2018 Nowak et al.
10,156,306 B2 12/2018 Fangrow
10,173,045 B2 1/2019 Mansour
10,179,203 B1 1/2019 Huslage et al.
10,315,025 B2 6/2019 Phillips et al.
10,398,887 B2 9/2019 Fangrow, Jr. et al.
10,441,507 B2 10/2019 Sanders
10,518,078 B2 12/2019 Stjernberg Bejhed et al.
10,569,073 B2 2/2020 Hallisey et al.
10,625,068 B2 4/2020 Leuthardt et al.
10,655,768 B2 5/2020 Jones et al.
10,697,570 B2 6/2020 Fangrow
10,744,315 B2 8/2020 Sanders
10,842,982 B2 11/2020 Fangrow, Jr.
10,857,346 B2 12/2020 Dennis et al.
10,864,362 B2 12/2020 Jones et al.
10,881,847 B2 1/2021 Lynn
11,168,818 B2 11/2021 Fangrow
11,207,514 B2 12/2021 Kakinoki
11,235,135 B2 2/2022 Tsai
11,273,297 B2 3/2022 Kakinoki
11,484,471 B2 11/2022 Sanders
11,491,084 B2 11/2022 Ueda et al.
2004/0215158 A1 10/2004 Anderson
2005/0090805 A1 4/2005 Shaw et al.
2006/0129109 A1 6/2006 Shaw et al.
2007/0088292 A1 4/2007 Fangrow, Jr.
2007/0088293 A1 4/2007 Fangrow, Jr.
2007/0088294 A1 4/2007 Fangrow, Jr.
2007/0225635 A1 9/2007 Lynn
2008/0039803 A1 2/2008 Lynn
2011/0106046 A1 5/2011 Hiranuma
2014/0246616 A1 * 9/2014 Fangrow ................ F16L 29/00 251/148
2014/0249487 A1 9/2014 Lynn
2014/0330254 A1 11/2014 Rosenberger et al.
2016/0000363 A1 1/2016 Jones et al.
2017/0036007 A1 * 2/2017 Hallisey ................ A61M 39/26
2018/0200147 A1 7/2018 Sanders
2019/0184152 A1 6/2019 Kakinoki
2019/0224468 A1 7/2019 Jones et al.
2019/0269899 A1 * 9/2019 McMichael ........... A61M 39/26
2019/0282797 A1 9/2019 Tsai
2020/0113784 A1 4/2020 Lopez et al.
2020/0179672 A1 6/2020 Kakinoki
2020/0215319 A1 7/2020 Fangrow, Jr. et al.
2020/0284385 A1 9/2020 Fangrow
2020/0323734 A1 10/2020 Ueda et al.
2020/0338331 A1 10/2020 Sanders
2021/0069484 A1 3/2021 Tsai
2021/0077803 A1 3/2021 Lynn
2021/0252267 A1 8/2021 Fangrow, Jr.
2021/0372551 A1 12/2021 Clark et al.
2021/0388926 A1 12/2021 Martin et al.
2021/0393938 A1 12/2021 Lynn et al.
2022/0032029 A1 * 2/2022 Lazzara ............. A61M 39/1011
2022/0146031 A1 * 5/2022 Lusso ..................... F16L 37/35
2022/0260189 A1 8/2022 Deuse
2022/0282814 A1 9/2022 Fangrow
2023/0001172 A1 * 1/2023 Wine .................... A61M 39/20
2023/0313928 A1 * 10/2023 Mansour ............... A61M 39/10 251/149

FOREIGN PATENT DOCUMENTS

EP 1622675 B1 8/2009
EP 2144634 A1 1/2010
EP 2298407 A1 3/2011
EP 2694132 A1 2/2014
EP 2562456 B1 6/2014
EP 2782633 A1 10/2014
EP 1842002 B1 4/2015

(56) References Cited

FOREIGN PATENT DOCUMENTS

| | | | |
|---|---|---|---|
| EP | 2736582 | B1 | 5/2015 |
| EP | 2089094 | B1 | 1/2016 |
| EP | 2219721 | B1 | 12/2017 |
| EP | 2753396 | B1 | 12/2017 |
| EP | 2736584 | B1 | 4/2018 |
| EP | 3305361 | A1 | 4/2018 |
| EP | 2271398 | B1 | 11/2018 |
| EP | 2480281 | B1 | 11/2018 |
| EP | 2790750 | B1 | 11/2018 |
| EP | 2331191 | B1 | 3/2019 |
| EP | 3079756 | B1 | 3/2019 |
| EP | 2121114 | B1 | 5/2019 |
| EP | 2719419 | B1 | 5/2019 |
| EP | 2956204 | B1 | 8/2019 |
| EP | 3421077 | B1 | 8/2019 |
| EP | 3530313 | A1 | 8/2019 |
| EP | 3538201 | A1 | 9/2019 |
| EP | 3570807 | A1 | 11/2019 |
| EP | 3570809 | A1 | 11/2019 |
| EP | 2536463 | B1 | 4/2020 |
| EP | 3381505 | B1 | 5/2020 |
| EP | 3538201 | B1 | 5/2020 |
| EP | 1904152 | B1 | 12/2020 |
| EP | 2150307 | B1 | 12/2020 |
| EP | 3313490 | B1 | 1/2021 |
| EP | 3760275 | A1 | 1/2021 |
| EP | 3851155 | A1 | 7/2021 |
| EP | 3517164 | B1 | 9/2021 |
| EP | 3954355 | A1 | 2/2022 |
| EP | 3960229 | A1 | 3/2022 |
| EP | 3973044 | A1 | 3/2022 |
| EP | 3305361 | B1 | 5/2022 |
| EP | 3134052 | B1 | 8/2022 |
| EP | 3530313 | B1 | 8/2022 |
| WO | WO-2021099437 | A1 | 5/2021 |
| WO | WO-2021180675 | A1 | 9/2021 |
| WO | WO-2021252197 | A1 | 12/2021 |
| WO | WO-2022042956 | A1 | 3/2022 |
| WO | WO-2022149339 | A1 | 7/2022 |
| WO | WO-2022207560 | A1 | 10/2022 |

OTHER PUBLICATIONS

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.

IVteam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 May 2021 Rev. 02.

Przen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

* cited by examiner

CONNECTOR COUPLING ASSEMBLY

CROSS-REFERENCE TO RELATED APPLICATION

This application claims the benefit of U.S. Provisional Patent Application No. 63/426,430 filed Nov. 18, 2022 entitled "Connector Coupling Assembly", which is incorporated by reference herein in its entirety.

FIELD OF THE INVENTION

The present disclosure generally relates to connectors, and, in particular, to connector couplings.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Often, tubing or catheters are coupled or secured to each other to allow fluid communication between various portions of tubing or catheters.

In some applications, such tubing or catheters may become dislodged due to improper securement and/or when the coupling is subject to forces greater than what the coupling is designed to withstand.

SUMMARY

One or more embodiments of the present invention are directed to a coupler including a first connector having a first end, a second end opposite the first end, and a first valve disposed between the first end and the second end, a second connector having a mating portion, a connecting portion opposite the mating portion, and a second valve disposed at least partially within the mating portion, and a collar having a body detachably coupled to the mating portion of the second connector and a releasing portion disposed opposite the body, the releasing portion configured to receive at least a portion of the first connector to detachably couple the first connector to the collar and the second connector such that the first end of the first connector is disposed within the second connector. The first connector is configured to decouple from the collar and the second connector and is prevented from re-coupling to the collar once decoupled.

In some embodiments, the first connector is configured to decouple from the collar in response to a pullout force exceeding a predetermined threshold force. The pullout force is a force applied to the first connector along a central axis of the first connector. The central axis extends at least along a length of the first connector. The central axis extends through the first connector, the collar, and the second connector when the first connector is coupled to the collar and the collar is coupled to the second connector.

In some embodiments, the first connector is configured to remain coupled to the collar when the pullout force does not exceed the predetermined threshold force.

In some embodiments, the releasing has a slot at least partially longitudinally extending along the collar. The slot is configured to allow the releasing portion to radially expand outwards. Upon decoupling of the first connector from the collar, the slot allows the releasing portion to flex radially inwards. The first valve is prevented from contacting the second valve when the slot is flexed radially inwards.

In some embodiments, the first connector includes a body having an interior space, the interior space housing the first valve. The first connector includes a biasing element disposed within the interior space, the biasing element coupled to the first valve.

In some embodiments, the first connector includes a guide and the collar includes a channel sized and shaped to receive the guide to prevent rotational movement of the first connector relative to the collar when the guide is disposed within the channel. The guide extends from an external surface of the first connector and the first connector includes a wedge extending from the external surface opposite the guide, the wedge sized and shaped to be received by a slot disposed on the collar.

In some embodiments, the collar includes a ring, and the ring includes a slot longitudinally extending through the collar. The ring includes a first ring portion and a second ring portion, and the slot is disposed between the first ring portion and the second ring portion. The collar includes a body coupled to the ring via a channel, the body being disposed proximate the connecting portion of the second connector and the ring being disposed proximate the first end of the first connector when the first connector and the second connector are coupled to the collar.

In some embodiments, the first valve is disposed proximate the second valve when the first connector is coupled to the collar.

In some embodiments, the second end of the first connector is disposed within the second connector when the first connector is coupled to the collar.

In some embodiments, the second end of the first connector is disposed within the mating portion of the second connector when the first connector is coupled to the collar.

In some embodiments, the first connector includes a wedge having a ramp and the collar includes a slot sized and shaped to receive the wedge such that the wedge is at least partially disposed within the slot when the first connector is coupled to the collar.

In some embodiments, the first connector includes a stopper configured to prevent axially movement of the collar to an area proximate the first end.

In some embodiments, wherein the second end of the first connector has a maximum diameter less than a maximum diameter of the mating portion of the second connector.

In some embodiments, the coupler has a first configuration and in the first configuration the first connector is disposed within the collar such that the collar is disposed between the first end and the second end. The coupler has a second configuration and in the second configuration the first connector is coupled to the collar and the collar is coupled to the second connector. The coupler has a third configuration and in the third configuration the first connector is disconnected from the collar and the collar is coupled to the second connector.

In some embodiments, the first connector is coupled to a first portion of tubing at the first end and the second connector is coupled to a second portion of tubing at the connecting portion.

In some embodiments, the mating portion has a maximum diameter greater than a maximum diameter of the connecting portion.

In some embodiments, the first end has a maximum diameter substantially the same as a maximum diameter of the second end.

In some embodiments, the second connector includes a pin disposed between the mating portion and the connecting portion, and the pin at least partially extends into the first valve when the first connector is coupled to the collar and the collar is coupled to second connector.

In some embodiments, a fluid pathway is formed between the connecting portion of the second connector and the first end of the first connector when the first connector is coupled to the collar and the collar is coupled to the second connector.

One or more embodiments of the present invention are directed to a coupler including a first connector having a first end, a second end opposite the first end, a central axis extending through at least the first end and the second end, a body disposed between the first end and the second end, and a first valve disposed proximate the second end, a second connector having a threaded mating portion, a connecting portion opposite the mating portion, a second valve disposed within the mating portion, and pin disposed at least partially within the mating portion, and a collar having a releasing portion detachably coupled to the first connector and a body detachably coupled to the mating portion of the second connector. The collar is configured to couple the first connector to the second connector such that at least the first end of the first connector is disposed within the second connector. The first connector is configured to decouple from the collar and the second connector in response to a pullout force exceeding a predetermined threshold force. The first connector is prevented from re-coupling to the second connector and the collar once decoupled.

One or more embodiments of the present invention are directed to a coupler including a first connector having a first end, a second end opposite the first end, a central axis extending through at least the first end and the second end, a body disposed between the first end and the second end, and a first valve disposed proximate the second end, the body having an interior space housing the first valve and a biasing element coupled to the first valve, a second connector having a threaded mating portion, a connecting portion opposite the mating portion, a second valve disposed within the mating portion, and pin disposed at least partially within the mating portion, and a collar having a releasing portion detachably coupled to the first connector and a body threadably coupled to the mating portion of the second connector, the releasing portion having a slot longitudinally extending through the releasing portion, the slot being configured to allow the releasing portion to expand radially outward to detachably couple the first connector to the releasing portion of the collar. The collar is configured to couple the first connector to the second connector such that at least the first end of the first connector is disposed within the second connector. The first connector is configured to decouple from the collar and the second connector in response to a pullout force exceeding a predetermined threshold force. The first connector is prevented from re-coupling to the second connector and the collar once decoupled. The central axis extends through the first connector, the collar and the second connector when the collar is coupled to the first connector and the second connector.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1A:
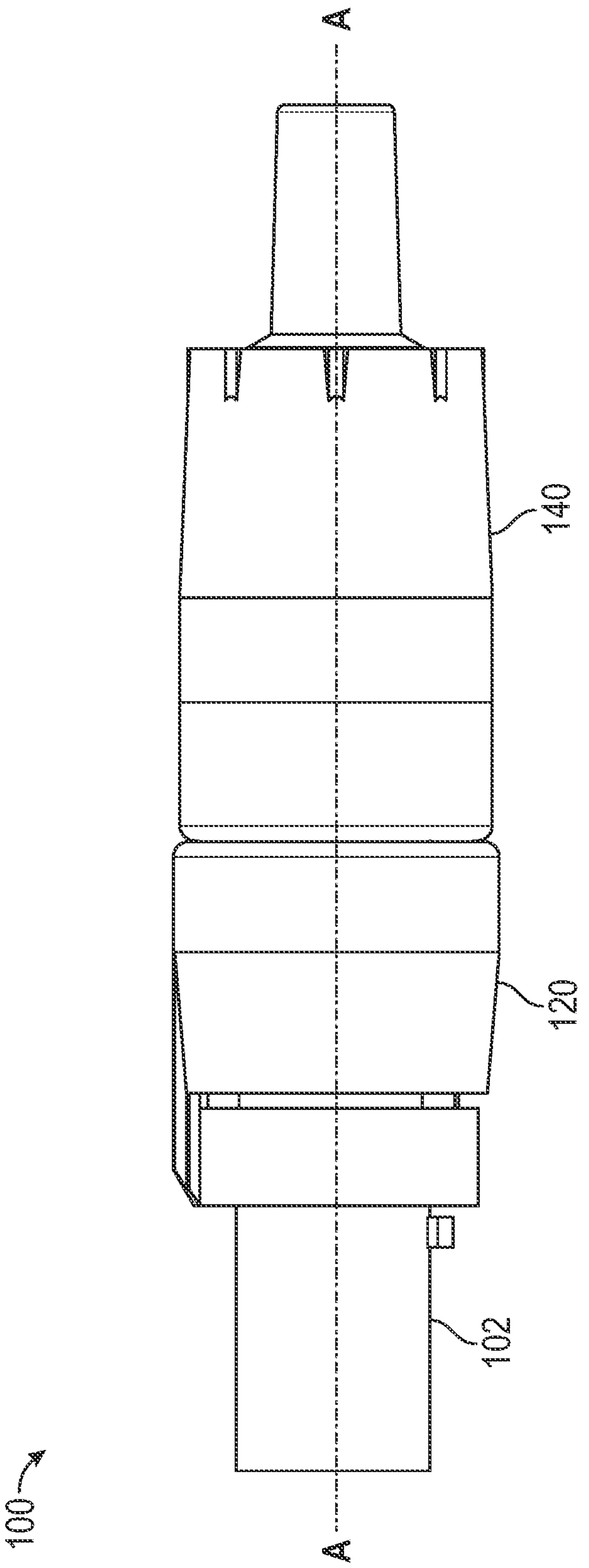
FIG. 1A is a side view of a coupler assembly, in accordance with various aspects of the present disclosure.

The disclosed coupler assembly includes a first connector, a collar, and a second connector. The collar is configured to couple the first connector to the second connector. The coupler assembly may have a first configuration, a second configuration, and a third configuration. In the first configuration, the first connector is coupled to the collar, and the first connector and the collar are decoupled from the second connector. In the second configuration, the first connector is coupled to the collar, which is also coupled to the second connector. In the third configuration, the first connector is decoupled from the collar, and the collar is coupled to the second connector.

The coupler assembly may be configured to couple a first portion of tubing to a second portion of tubing. For example, the first portion of tubing may be coupled to the first connector and the second portion of tubing may be coupled to the second connector. The first portion of tubing and/or the second portion of tubing may also couple to a patient or fluid source. In some embodiments, the coupler assembly allows for the flow of fluid from the first portion of tubing to the second portion of tubing. For example, the collar may couple the first connector to the second connector such that a fluid pathway is formed through the first connector and the second connector to allow the flow of fluid from the first portion of tubing through the first connector and the second connector to the second portion of tubing. The fluid pathway may allow for the flow of fluid from the second portion of tubing through the second connector and the first connector to the first portion of tubing.

In some embodiments, the collar is configured to allow the first connector to decouple from the second connector. For example, the collar may couple the first connector to the second connector and may be configured to allow the first connector to decouple from the collar and the second connector due to a disconnection event. The collar may allow for one way connection of the first connector to the connecter. The first connector may be discarded and replaced with a new sterile connector to prevent infection or contamination that can occur if the first connector is re-used (e.g., coupled again to the collar and the second connector). In some embodiments, the first connector is configured to decouple based on a force that exceeds a predetermined threshold force. When a force is applied to the first connector, such as a pullout force, that exceeds the predetermined threshold force, the first connector may decouple from the collar and the second connector. The pullout force may be a force that occurs along the longitudinal axis of the first connector. In some embodiments, the pullout force is caused by tugging or pulling on the first portion of tubing coupled to the first connector. Alternatively, the pullout out force applied to the first connector may be caused by tugging or pulling on the second connector and/or the second portion of tubing coupled to the second connector.

In some embodiments, once the first connector is decoupled from the collar and the second connector, the first connector is configured to not be re-coupled to the collar. For example, once the first connector decouples from the collar, the first connector may not be able to re-couple to the collar to prevent attachment of the first connector the collar and valve after a disconnection event. The collar may include a slot that allows the first connector to couple to the collar. The slot may have an open configuration and a closed configuration. The slot may be in the open configuration when the first connector is coupled to the collar. Upon the first connector decoupling from the collar, and the second connector, the slot may move to the closed configuration and thereby prevent the first connector from coupling with the collar.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for case of understanding. Reference numbers may have letter suffixes appended to indicate separate instances of a common element while being referred to generically by the same number without a suffix letter.

While the following description is directed to the connection of medical fittings for the administration of medical fluid using the disclosed coupler, it is to be understood that this description is only an example of usage and does not limit the scope of the claims. Various aspects of the disclosed coupler may be used in any application where it is desirable to secure the connection of various tubing and fittings.

The disclosed coupler assembly overcomes several challenges discovered with respect to certain conventional couplers. One challenge with certain conventional couplers is that certain conventional couplers may be improperly secured. Further, during use, certain conventional couplers may be designed to release or dislodge in response to relatively low pullout forces. For example, certain conventional couplers may release in response to pullout forces experienced during patients rolling over in bed, patients catching tubing or lines on bed rails, moving patients to a different bed, fidgeting by pediatric patients, and/or disoriented adult patients pulling out their lines. Indeed, the Association for Vascular Access (AVA) Annual Scientific Meeting in 2017 reported a 10% dislodgement rate for 1,000 patients fitted with peripheral IV catheters, translating to approximately 33 million dislodgements per year in the U.S. alone. Because the accidental or unintentional dislodgement of tubing, catheters, or fittings may interrupt the administration of medical fluids, the use of certain conventional couplers is undesirable.

Further, conventional couplers may allow for re-attachment of a connector to a valve or another connector after a disconnection event. Re-attachment after a disconnection event can lead to infection. For example, conventional couplers may include two connectors (e.g., valves, connectors, couplers, tubes, etc.) coupled together to provide a fluid pathway from a fluid source to a patient. The two connectors of the conventional coupler may be de-coupled from each other due to a disconnection event and may result in on one or both of the connectors contacting the floor, another patient, another bed, or another individual which can result in contaminants (e.g., debris, bacteria, viruses, or other harmful elements) being disposed on the first connector. Conventional couplers may allow the connectors to be re-coupled resulting in an increased risk of infection due to contaminants entering the fluid pathway.

Therefore, in accordance with the present disclosure, it is advantageous to provide couplers and coupler/connector assemblies as described herein that allows for improved securement of fittings or connectors. The disclosed couplers and coupler/connector assemblies are structured as described herein so as to permit the secure retention of the connectors, while preventing re-coupling of the connectors after a disconnection event.

Figure 1B:
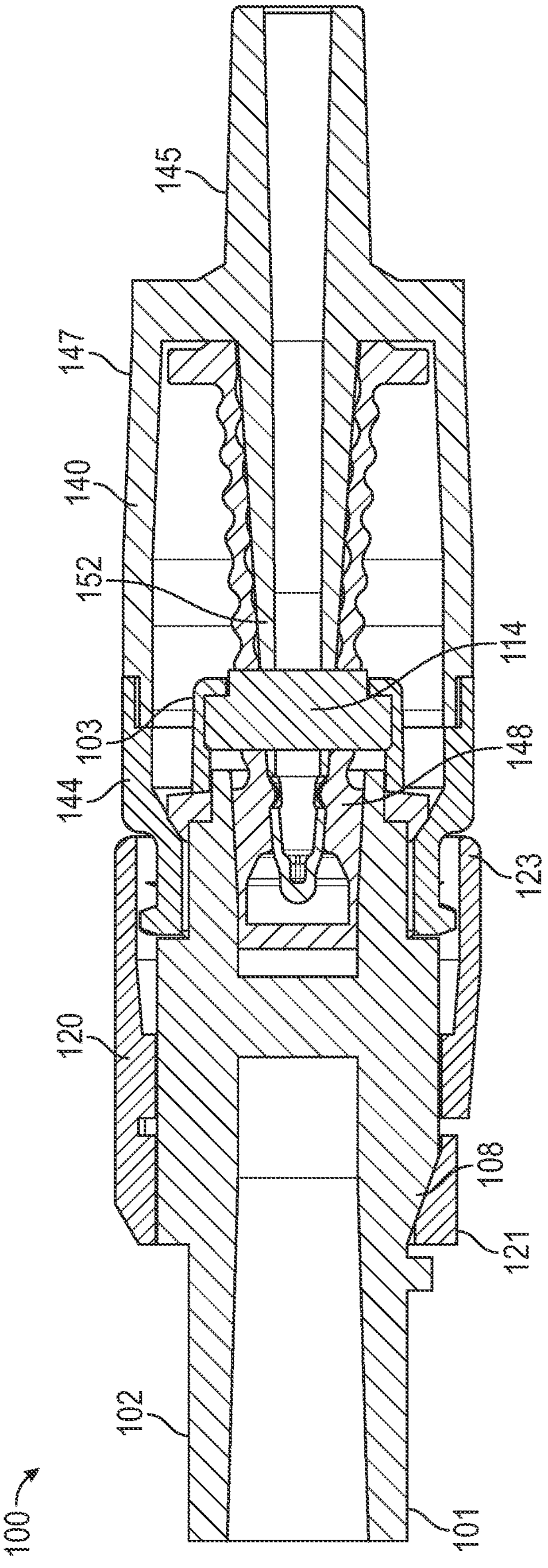
FIG. 1B is a cross sectional side view of the coupler assembly of FIG. 1A.
Figure 1C:
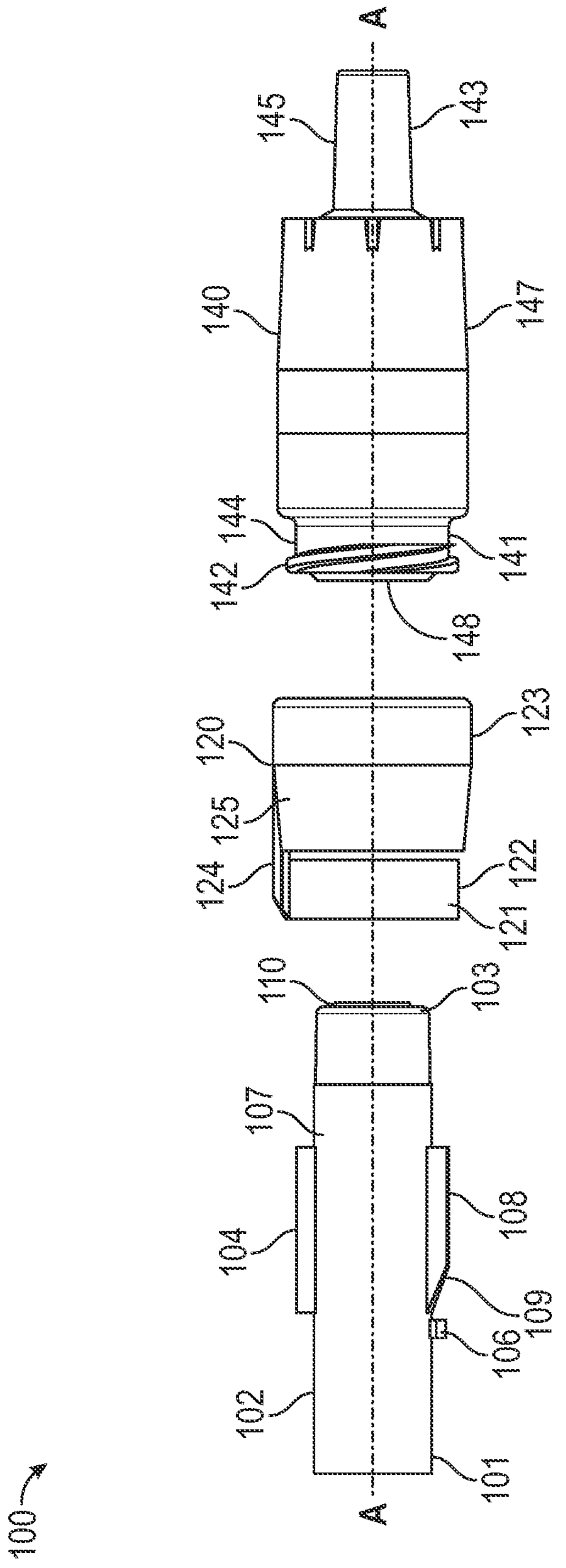
FIG. 1C is an exploded side view of the coupler assembly of FIG. 1A showing a first connector, a collar, and a second connector.

FIG. 1A is a side view of a coupler assembly, in accordance with various aspects of the present disclosure. FIG. 1B is a cross sectional side view of the coupler assembly of FIG. 1A. FIG. 1C is an exploded side view of coupler assembly of FIG. 1A showing a connector, a collar, and a valve.

With reference to FIGS. 1A-1C, coupler assembly 100 allows the flow of a fluid, such as a medical fluid, from a fluid source to a patient by releasably coupling a portion of tubing or line with another portion of tubing or line in fluid communication. Coupler assembly 100 may be referred to as coupler or connector coupler assembly. Coupler assembly 100 may include first connector 102, collar 120, and second connector 140. Collar 120 may be configured to couple first connector 102 to second connector 140. In the depicted example, portions of tubing can be terminated with connectors/valves, such as first connector 102 and/or second connector 140. In some embodiments, coupler assembly 100 includes central axis A-A and first connector 102, collar 120, and second connector 140 are coupled in series along central axis A-A. First connector 102 and/or second connector 140 may allow for the connection and/or disconnection of tubing to allow for selective fluid communication therebetween. Central axis A-A may extend longitudinally along the length of first connector 102, collar 120, and second connector 140.

In some embodiments, first connector 102 is coupled to second connector 140 via collar 120. Collar 120 may be configured to detachably couple first connector 102 to second connector 140 such that a portion of first connector 102 is disposed within second connector 140. Collar 120 may be configured to allow for one way connection of first connector 102 to collar 120. For example, collar 120 may be configured to prevent re-coupling of first connector 102 to collar 120 once first connector 102 is decoupled from collar 120. Collar 120 may be configured to allow one way connection of first connector 102 to collar 120.

In some embodiments, first connector 102 is coupled to a first portion of tubing to allow the first portion of tubing to be connected and/or disconnected with second connector 140. First connector 102 may include first end 101 and second end 103. First end 101 may be coupled to tubing (e.g., a first portion of tubing) and second end 103 may be configured to couple to collar 120. In some embodiments, a portion of tubing can be coupled with, or engage with first end 101 of first connector 102. First connector 102 via first end 101 may be in fluid communication with the tubing to allow fluid to pass through first connector 102. In some embodiments, first end 101 can have a flat surface to allow for clinicians to easily clean and disinfect first end 101. First end 101 may be in fluid connection with second end 103. First end 101 and second end 103 may be disposed along the longitudinal length of first connector 102. For example, first end 101 and second 103 may be disposed along central axis A-A. First end 101 and/or second end 103 may include an opening to allow first end 101 and/or second end 103 to be in fluid communication with one or more elements (e.g., tubing, connectors, valves, collars, attachments, etc.). For example, first end 101 may be coupled to a tube and second end 103 may include opening 110 to allow for fluid communication through first connector 102. In some embodiments, first connector 102 includes valve 114 (FIG. 5), which is at least partially disposed within opening 110.

In some embodiments, fluid can exit or flow through first connector 102 via second end 103 disposed opposite to first end 101. The flow path through first connector 102 can have a straight fluid pathway to make flushing easier and to reduce the risk of hemolysis. Optionally, first connector 102 can include features (e.g., raised features, gripping features) disposed on the outer surface of first connector 102 to allow a clinician to more easily handle or manipulate first connector 102. Some embodiments of first connector 102 may provide connectors that are compatible with connectors of other portions of fluid delivery systems. First connector 102 may be substantially cylindrically shaped.

In some embodiments, first connector 102 includes guide 104, stopper 106, and wedge 108. Stopper 106 may be disposed proximate wedge 108. In some embodiments, stopper 106 is disposed between first end 101 and wedge 108. Stopper 106 may be disposed proximate to first end 101 compared to wedge 108 and wedge 108 may be disposed proximate second end 103 compared to stopper 106. Stopper 106 has a length substantially less than wedge 108 and stopper 106 has a width substantially the same as wedge 108. In some embodiments, stopper 106 and wedge 108 extend away from central axis A-A and are disposed on external surface 107 of first connector 102. Wedge 108 may include ramp 109. Ramp 109 may be disposed proximate stopper 106. In some embodiments, ramp 109 slopes towards external surface 107 proximate stopper 106.

Guide 104 may be disposed from external surface 107 and may be extend away from central axis A-A. In some embodiments, guide 104 and wedge 108 have approximately the same length. Guide 104 may extend from external surface 107 opposite where wedge 108 extends from external surface 107. In some embodiments, guide 104 is substantially rectangular shaped. Alternatively, guide 104 may be trapezoidal, circular, semi-circular, triangular, or any other shape desired. In some embodiments, guide 104 is disposed substantially equidistant from first end 101 and second end 103.

Similarly, a second portion of tubing can be terminated by second connector 140 to allow the second portion of tubing to be connected and/or disconnected from collar 120 via second connector 140. Second connector 140 may include first end 141 and second end 143 disposed opposite first end 141. First end 141 may include mating portion 144 and second end 143 may include connecting portion 145, which may be disposed opposite mating portion 144. In some embodiments, a portion of tubing is coupled with, or engaged with connecting portion 145 of second connector 140. In some embodiments, connecting portion 145 includes a threaded connection to facilitate coupling with tubing. For example, connecting portion 145 may include connecting portion 145 configured to couple to a portion of tubing.

In some embodiments, mating portion 144 includes features (e.g., threads) that allow for second connector 140 to mate with collar 120. Mating portion 144 may fit together or otherwise engage with second end 123 of collar 120 to allow fluid communication between first connector 102 and second connector 140 and the portions of tubing coupled thereto when first connector 102 is coupled to collar 120. As can be appreciated, first connector 102 and second connector 140 can be coupled and decoupled via collar 120 to permit fluid communication as desired. As can be appreciated, first connector 102 can detachably couple with second connector 140 via collar 120 to provide needle free connections. Advantageously, first connector 102 may pair with second connector 140 via collar 120 to form a leak-free closed system, allowing the delivery of various drugs or fluids.

In some embodiments, second connector 140 includes housing 147 and mating portion 144. Housing 147 may be disposed between first end 141 (e.g., mating portion 144) and second end 143 (e.g., connecting portion 145). In some embodiments, housing 147 is disposed between mating portion 144 and connecting portion 145. In some embodiments, mating portion 144 is coupled to housing 147, which is coupled to connecting portion 145. Housing 147 may have a maximum diameter greater than the maximum diameter of each of mating portion 144 and connecting portion 145. In some embodiments, mating portion 144, housing 147, and connecting portion 145 form a unitary structure. Mating portion 144 may be disposed proximate first end 141. Mating portion 144 may include threads configured to couple second connector 140 to collar 120 (e.g., body 125). Alternatively, mating portion 144 may include fasteners, adhesives, magnets, or other components to configured to couple second connector 140 to collar 120. In some embodiments, collar 120 may be secured to second connector 140 by engaging with mating portion 144.

Second connector 140 may include valve 148, which is configured to control the flow of fluid. For example, second connector 140 may be coupled to a second portion of tubing and may include valve 148 that is configured to control the flow of fluid to or from the second portion of tubing to first connector 102 coupled to second connector 140. In some embodiments, valve 148 has an open configuration and closed configuration. In the open configuration, valve 148 may be configured to allow fluid to flow from first end 141 to second end 143, or vice versa. In the closed configuration, valve 148 may be configured to block or prevent the flow of fluid in or out of first end 141 (e.g., mating portion 144) and/or second end 143 (e.g., connecting portion 145). In some embodiments, valve 148 is in the open configuration when first connector 102 is coupled to second connector 140 via collar 120. Valve 148 may be in the closed position upon disconnecting or decoupling of first connector 102 from second connector 140 and/or collar 120.

Referring to FIGS. 1B-1C, when first connector 102 is coupled to second connector 140 via collar 120, valve 114 of first connector 102 is proximate to or disposed within valve 148 of second connector 140. When first connector 102 is coupled to second connector 140 via collar 120, first connector 102 may be at least partially disposed within second connector 140 such that a pin (e.g., pin 152) within second connector 140 extends into valve 114. In some embodiments, when first connector 102 is coupled to second connector 140, a portion of first connector 102 may extend into and be disposed within second connector 140. Second connector 140 may include pin 152 (FIG. 6) that may be disposed within valve 114 when first connector 102 is coupled to second connector 140 allowing for a fluid pathway between first connector 102 and second connector 140 via valve 114 and pin 152. Pin 152 may be configured to extend through opening 150 (FIG. 6) of valve 148. In some embodiments, when first connector 102 is coupled to second connector 140, valve 148 is disposed within valve 114 and pin 152 extends into valve 114 and thus into first connector 102 allowing fluid to flow from within pin 152 of second connector 140, through valve 114 and into first connector 102. In some embodiments, when first connector 102 is coupled to second connector 140, a portion of valve 148 and/or pin 152 is disposed between valve 114 and first end 101 of first connector 102. Valve 114 may be disposed between first end 141 of second connector 140 and second end 103 of first connector 102 when first connector 102 is coupled to second connector 140.

In some embodiments, second connector 140 includes a sealing valve (e.g., valve 148) to allow for flow to pass therethrough when second connector 140 is coupled to first connector 102 via collar 120 and can prevent or restrict flow when first connector 102 is decoupled from collar 120. In some embodiments, second connector 140 includes a sealing valve to seal the flow path between first end 141 and second end 143 when first connector 102 is decoupled from collar 120. The sealing valve can be in an open position when first connector 102 is coupled to collar 120 and collar 120 is coupled to second connector 140, allowing flow between first connector 102 and second connector 140 via collar 120.

In some embodiments, second connector 140 is coupled to tubing that is in fluid communication with connecting portion 145 to allow the tubing to receive flow passing through second connector 140. Second connector 140 can receive fluid flow from first end 141 (e.g., mating portion 144) disposed opposite to second end 143 (e.g., connecting portion 145) or vice versa. In some embodiments, second connector 140 includes a no-drip feature to prevent leaks or surface contamination. Second connector 140 may further include a luer lock to prevent accidental discharges.

Similarly, first connector 102 can include a sealing valve to allow for flow to pass therethrough when first connector 102 is coupled to collar 120 and can prevent or restrict flow when connector is decoupled from collar 120. First connector 102 may include a sealing valve to seal the flow path between first end 101 and second end 103 when first connector 102 is uncoupled from collar 120. Further, the sealing valve may be in an open position when first connector 102 is coupled to collar 120, allowing flow into first connector 102 and between first end 101 and second end 103. Some embodiments provide that portions of the sealing valve can be formed from silicone.

Referring to FIGS. 1A-1C, second connector 140 may be coupled to first connector 102 via collar 120. Collar 120 may include first end 121 and second end 123. First end 121 of collar 120 may be configured to couple to first connector 102 and second end 123 of collar 120 may be configured to couple to second connector 140. In some embodiments, first end 121 of collar 120 couples to second end 103 of first connector 102 and second end 123 of collar 120 couples to first end 141 (e.g., mating portion 144) of second connector 140. Second end 123 of collar 120 may be configured to couple to mating portion 144 of second connector 140. In some embodiments, second end 123 includes threads disposed on an interior surface of collar 120, which are configured to mate with threads disposed on mating portion 144 of second connector 140 to secure collar 120 to second connector 140.

In some embodiments, collar 120 includes body 125, channel 124 and ring or releasing portion 122. Channel 124 may be configured to couple ring 122 to body 125. In some embodiments, channel 124 is sized and shaped to receive guide 104 of first connector 102. For example, when collar 120 is coupled to first connector 102, guide 104 may be disposed within in channel 124 to prevent rotation of first connector 102 relative to collar 120 when first connector 102 is coupled to collar 120.

Figure 4:
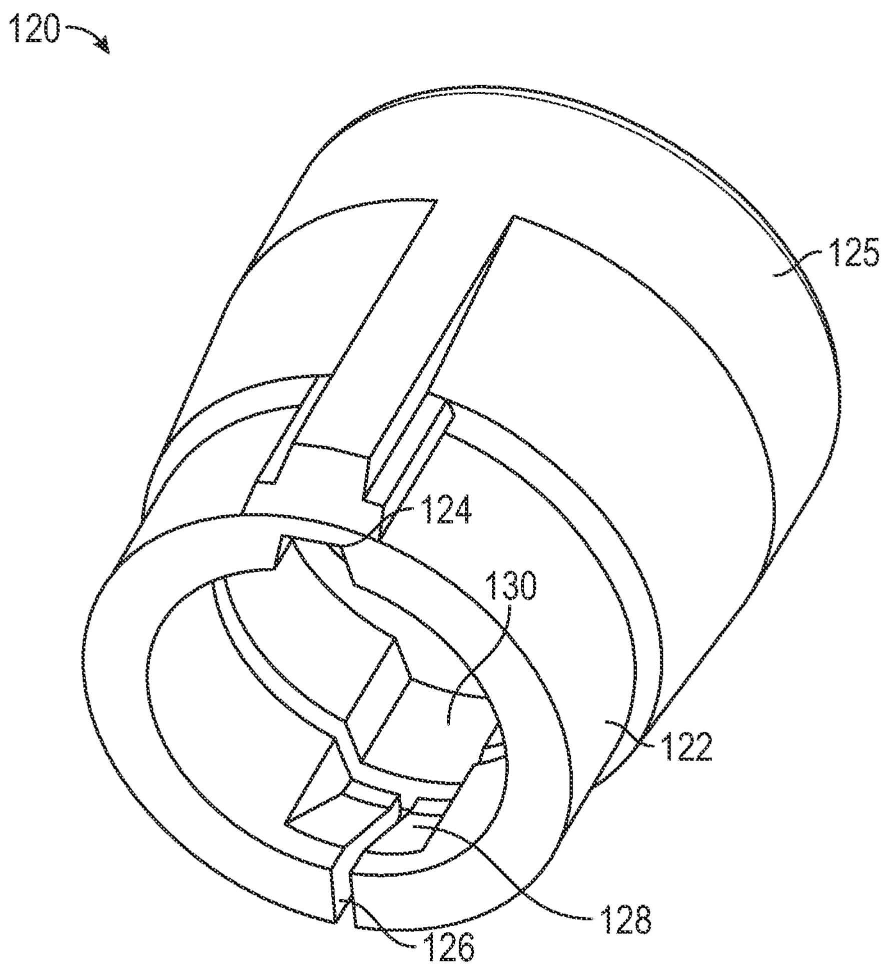
FIG. 4 is top perspective view of the collar of the coupler assembly of FIG. 1A, in accordance with some embodiments of the present disclosure.
Figure 5A:
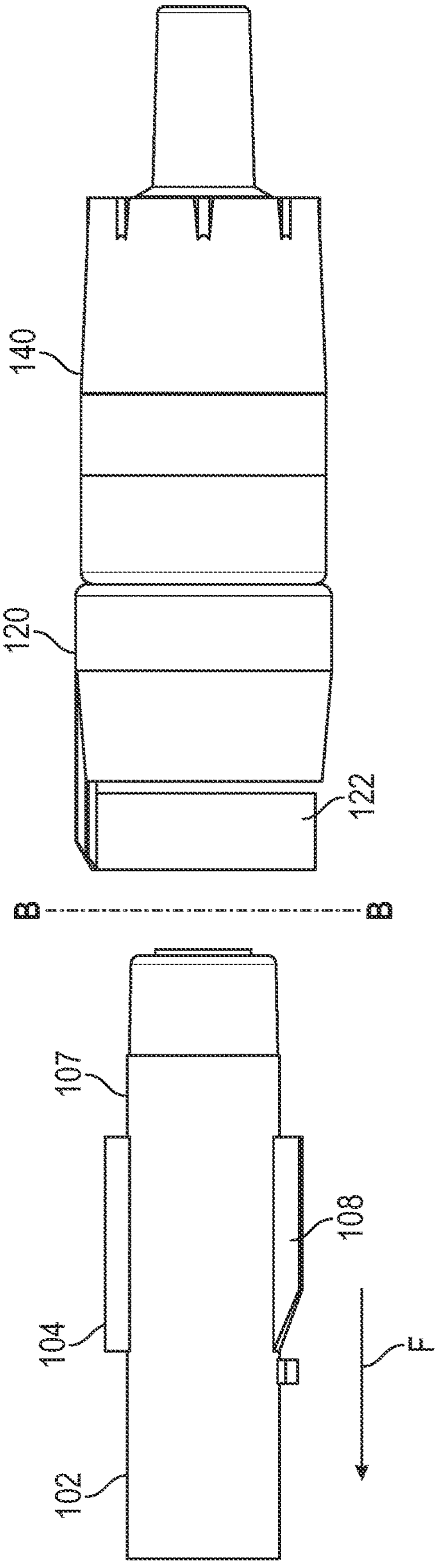
FIG. 5A is side view of the coupler assembly of FIG. 1A with the first connector decoupled from the collar and the second connector, in accordance with some embodiments of the present disclosure.
Figure 5B:
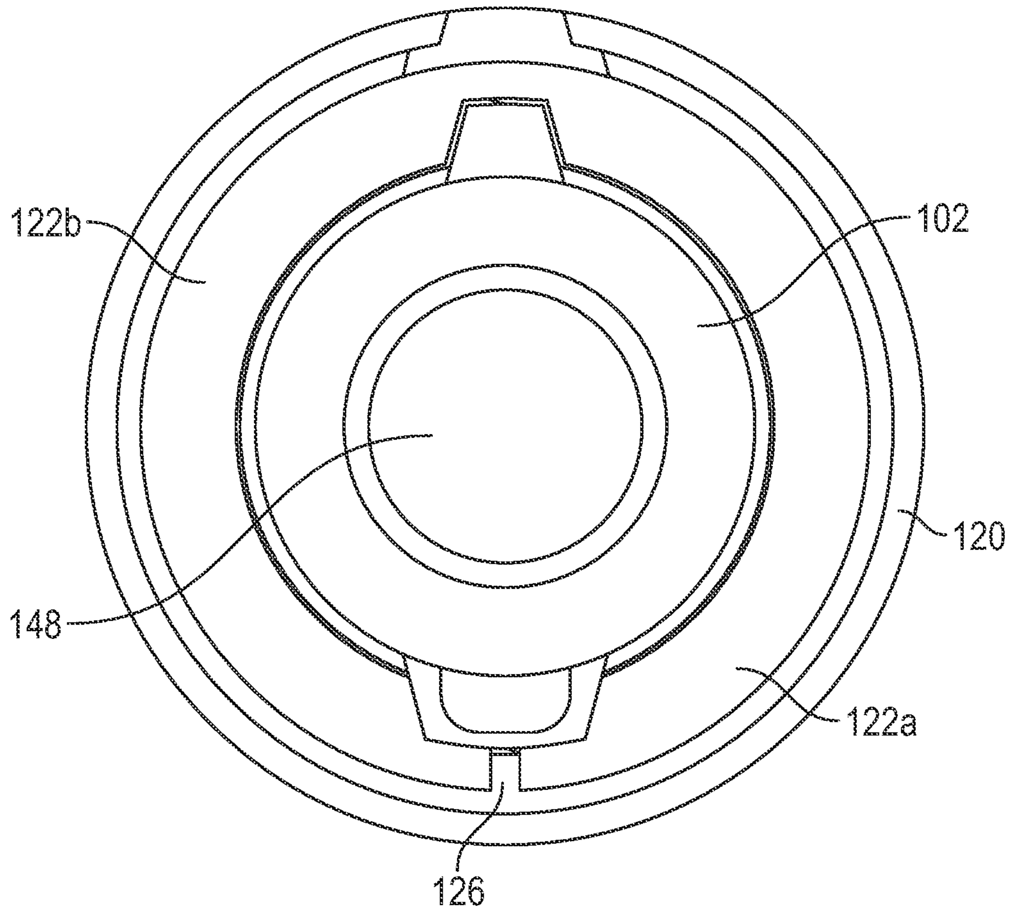
FIG. 5B is a cross-sectional view of the coupler assembly of FIG. 5A across plane B-B.

In some embodiments, ring 122 includes slot 126 (shown in FIGS. 4 and 5B). Slot 126 may extend longitudinally through ring 122. Slot 126 may be configured to receive wedge 108 of first connector 102. When first connector 102 is coupled to collar 120, wedge 108 may be disposed through slot 126 such that wedge 108 extends through slot

126 and into body 125. Body 125 may include a channel configured to receive wedge 108. In some embodiments, body 125 includes a channel to secure wedge 108 and prevent rotational movement of first connector 102 relative to collar 120. In some embodiments, when first connector 102 is coupled to collar 120, wedge 108 extends from first end 121 of collar 120 to a portion of collar 120 proximate second end 123. Ring 122 and slot 126 may be configured to allow for one way connection of first connector 102 to collar 120 and prevent connection of first connector 102 to collar 120 once first connector 102 is decoupled from collar 120.

In some embodiments, ring or releasing portion 122 includes first ring portion 122*a* and second ring portion 122*b* (FIG. 3B). First ring portion 122*a* may be coupled to second ring portion 122*b* at a top of ring 122. Slot 126 may be formed between first ring portion 122*a* and second ring portion 122*b* opposite where first ring portion 122*a* couples to second ring portion 122*b*. In other words, slot 126 may be formed due to first ring portion 122*a* being spaced apart from second ring portion 122*b*. In some embodiments, first ring portion 122*a* and second ring portion 122*b* are configured to radially deflect in response to a force (e.g., a pullout force exceeding a predetermined threshold). Ring 122 may be spaced apart from body 125 to allow first ring portion 122*a* and second ring portion 122*b* to radially deflect without body 125 radially deflecting.

In some embodiments, slot 126 has an open position and a closed position. Slot 126 may be in the open position due to first ring portion 122*a* being spaced apart from second ring portion 122*b*. For example, slot 126 may be in the open position when first ring portion 122*a* and second ring portion 122*b* radially deflect. In some embodiments, slot 126 is in the closed position when first ring portion 122*a* contacts or abuts second ring portion 122*b* thereby closing slot 126. Slot 126 may be in the open position when wedge 108 is disposed within or through slot 126. In some embodiments, wedge 108 is configured to keep slot 126 in the open position. In some embodiments, wedge 108 can only pass through slot 126 when slot 126 is in the open position. Slot 126 may be in the closed position when wedge 108 is removed from the slot 126.

In some embodiments, slot 126 is configured to go from the open position to the closed position. Once in the closed position, slot 126 may not easily go back to the open position. As discussed further below, removal of wedge 108 causes slot 126 to go from the open position to the closed position. Once in the closed position, first connector 102 may not be able to couple to collar 120 since wedge 108 can longer pass through slot 126. Ring 122 may have a biasing force the biases slot 126 to be in the closed position. In some embodiments, removal of wedge 108 from slot 126 results in slot 126 moving to the close deposition due to the biasing force of ring 122.

Figure 2A:
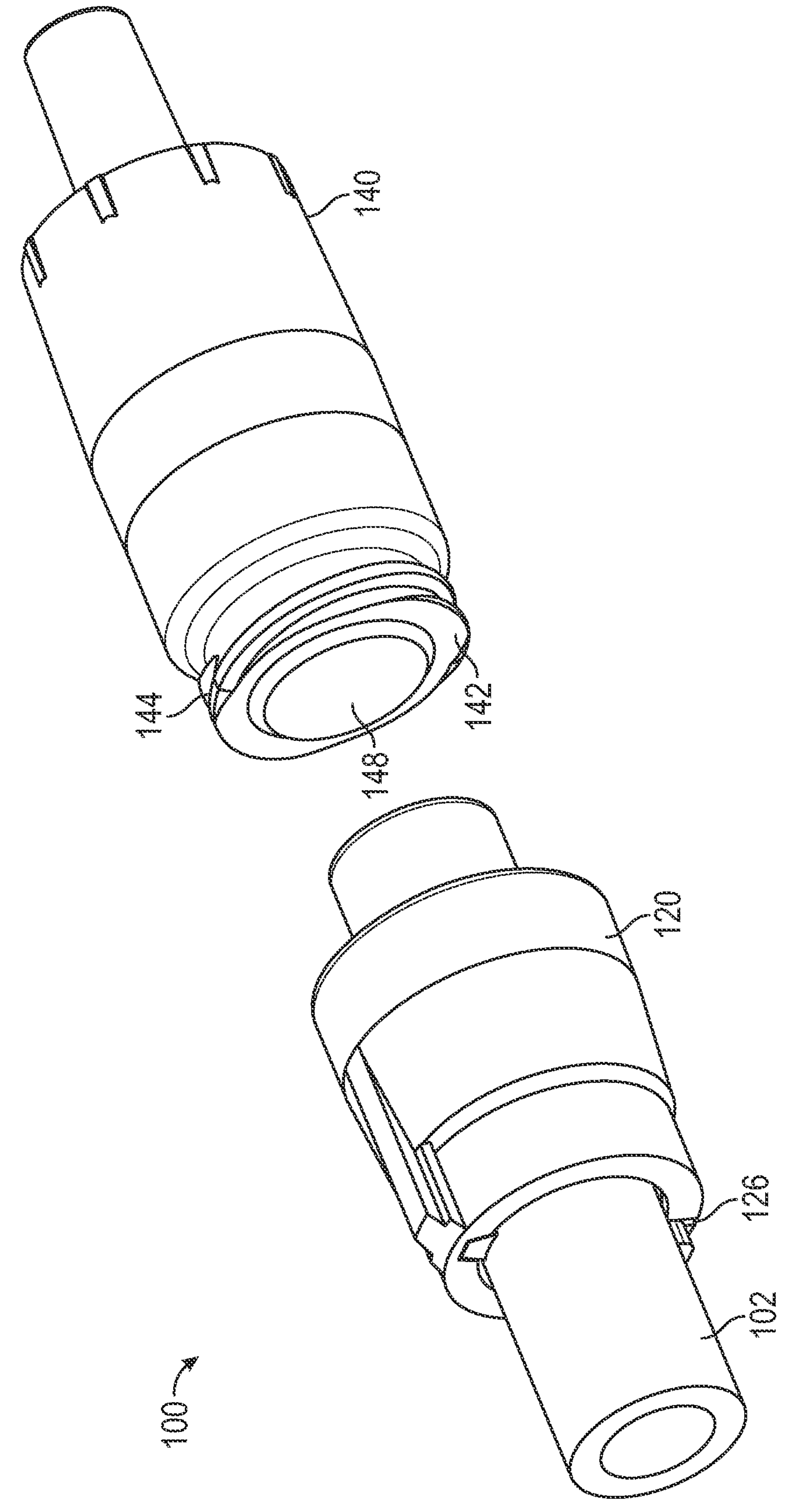
FIG. 2A is a perspective view of the coupler assembly of FIG. 1A with the collar coupled to the first connector, in accordance with some embodiments of the present disclosure.
Figure 2B:
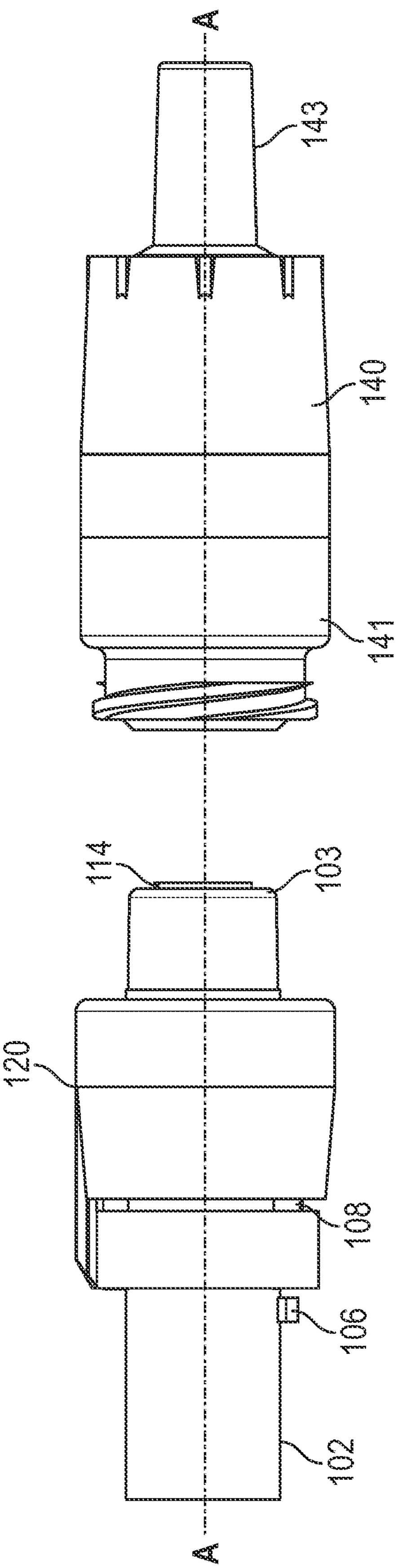
FIG. 2B is a side view of the coupler assembly of FIG. 2A.

FIG. 2A is an exploded perspective view of the coupler assembly of FIG. 1A with the collar coupled to the first connector, in accordance with some embodiments of the present disclosure. FIG. 2B is an exploded side view of the coupler assembly of FIG. 2A.

Referring to FIGS. 2A-2B, coupler assembly 100 may be configured to be in a first configuration. In the first configuration, first connector 102 may be coupled to collar 120, and first connector 102 and collar 120 may be decoupled or disconnected from second connector 140. In some embodiments, coupler assembly 100 is shipped or transported in the first configuration. Shipping or transporting coupler assembly 100 in the first configuration may prevent inadvertent compression of valve 148. For example, when first connector 102 is coupled to second connector 140 via collar 120, valve 148 of second connector 140 may be compressed (e.g., by first connector 102). In the first configuration, first connector 102 is decoupled or disconnected from second connector 140 resulting in first connector 102 not abutting or being proximate to valve 148 allowing valve 148 to be substantially decompressed. Accordingly, shipping or transporting coupler assembly 100 in the first configuration allows valve 148 to remain decompressed and thereby ends the life of valve 148.

In the first configuration, first connector 102 is disposed through collar 120 along central axis A-A. First connector 102 may be disposed through collar 120 such that collar 120 is disposed between first end 101 and second 103. In some embodiments, collar 120 is proximate second end 103 compared to first end 101. Collar 120 may be coupled to first connector 102 such that wedge 108 is disposed through slot 126. In some embodiments, first connector 102 is disposed within collar 120 such that wedge 108 extends from first end 121 to second end 123. In other words, first connector 102 may be disposed within collar 120 such that wedge 108 extends through ring 122 via slot 126 and into body 125.

In some embodiments, guide 104 is disposed within channel 124. Wedge 108 being disposed within slot 126 and extending into body 125 (e.g., via a channel within body 125) and guide 104 being disposed within channel 124 may prevent rotation of collar 120 relative to first connector 102.

In some embodiments, collar 120 is prevented from axially moving, relative to first connector 102, along central axis A-A towards first end 101 by stopper 106. Stopper 106 may be configured to prevent collar 120 from axially moving relative to first connector 102. Stopper 106 may be proximate first end 121 of collar 120 when first connector 102 is coupled to and disposed within collar 120. Collar 120 may be configured to axially move relative to first connector 102 towards second end 103 such that second end 103 is disposed within collar 120, but collar 120 may be prevented by stopper 106 from axially moving towards first end 101 such that first end 101 is disposed within collar 120.

Figure 3:
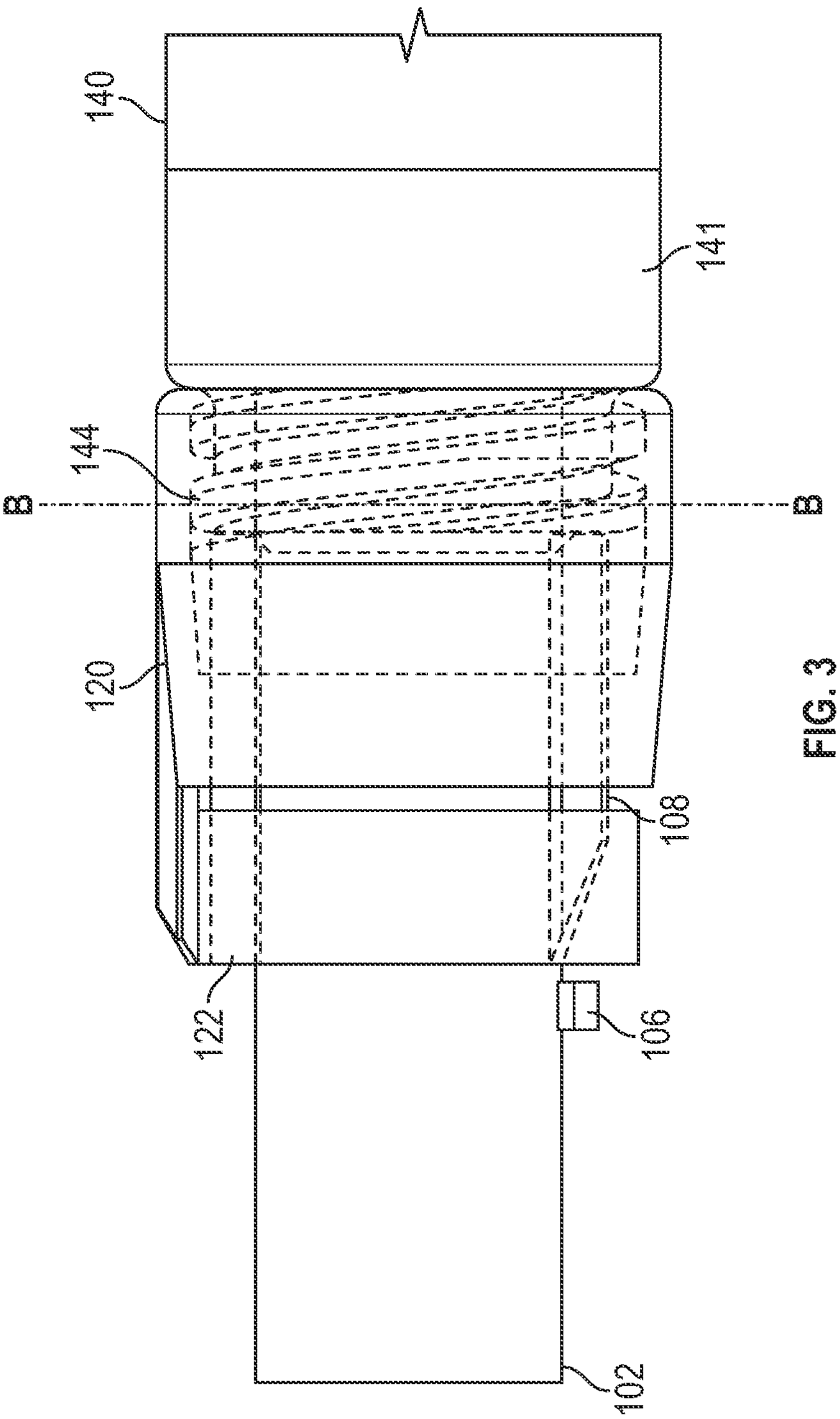
FIG. 3 is zoomed in view of the coupler assembly of FIG. 1A, in accordance with some embodiments of the present disclosure.

FIG. 3 is a close up view of the coupler assembly of FIG. 1A, in accordance with some embodiments of the present disclosure. FIG. 4 is top perspective view of the collar of the coupler assembly of FIG. 1A, in accordance with some embodiments of the present disclosure.

Referring to FIGS. 1A and 3-4, coupler assembly 100 may be configured to be in a second configuration. In the second configuration, mating portion 144 of second connector 140 is coupled to body 125 of collar 120 to secure second connector 140 to collar 120. In some embodiments, when first connector 102 is disposed through collar 120, second connector 140 is coupled to collar 120 (e.g., at mating portion 144) such that first connector 102 is at least partially disposed within second connector 140. Coupler assembly 100 may transition from the first configuration to the second configuration by coupling second end 123 of collar 120 to mating portion 144 of second connector 140.

Referring to FIG. 4, collar 120 may include inclined surface 128 and channel 130. Inclined surface 128 and channel 130 may be configured to contact wedge 108 when first connector 102 is disposed within and coupled to collar 120. In some embodiments, inclined surface 128 is disposed within ring 122 and channel 130 is disposed within body 125. Alternatively, ring 122 and body 125 are a unitary structure such that channel 130 is in communication with inclined surface 128. Inclined surface 128 may be sized and shaped to abut ramp 109 of wedge 108 when collar 120 is secured to first connector 102. A portion of wedge 108 may abut or be disposed within wedge channel 130.

In some embodiments, when first connector 102 is disposed within collar 120 and collar 120 is coupled to mating portion 144 of second connector 140 such that first connector 102 is at least partially disposed within second connector 140, a fluid pathway is formed along central axis A-A through first connector 102 and second connector 140. The fluid pathway may allow for the flow of fluid from a first portion of tubing coupled to first connector 102 to a second portion of tubing coupled to second connector 140.

In some embodiments, when first connector 102 is disposed within collar 120 and first end 121 of collar 120 is proximate stopper 106, ramp 109 may abut slot 126. In some embodiments, wedge 108 is inserted through slot 126 such that ramp 109 abuts slot 126 and slot 126 partially closes around ramp 109. For example, slot 126 may initially be in the open position as wedge 108 is inserted through slot 126 and collar 120 axially moves towards first end 101 of first connector 101. As collar 120 approaches stopper 106 and slot 126 approaches ramp 109, slot 126 may be configured to partially close to tighten around ramp 109.

In some embodiments, inclined surface 128 is configured to abut ramp 109 when first connector 102 is inserted into collar 120. Inclined surface 128 may assist with keeping wedge 108 disposed within slot 126 and thus assist in securing first connector 102 to collar 120. In some embodiments, as collar 120 axially moves towards first end 101 of connector 102 and begins to abut stopper 106, inclined surface 128 of slot 126 may abut or contact ramp 109 and wedge 108 may be secured within collar 120. Inclined surface 128 may be configured to cause slot 126 to at least partially open or transition from the closed position to the open position as first connector 102 is decoupled from collar 120.

First connector 102 may be secured with collar 120, and thus securely coupled to second connector 140, when wedge 108 is disposed within slot 126 (e.g., inclined surface 128 and channel 130). When wedge 108 is disposed within slot 126, first ring portion **122*a* and second ring portion 122*b* may be biased radially inward (e.g., biased to have slot 126 in the closed position). Slot 126 may remain in the open position due to wedge 108 being disposed within slot 126 and wedge 108 having a width greater than slot 126. First connector 102 may be coupled and secured to collar 120 due to wedge 108 being secured within slot 126. Wedge 108 is secured within slot 126 due to first ring portion 122*a* and second ring portion 122*b* providing compressive forces to wedge 108 and securing wedge 108 within slot 126 (e.g., inclined surface 128 and channel 130**).

Figure 5C:
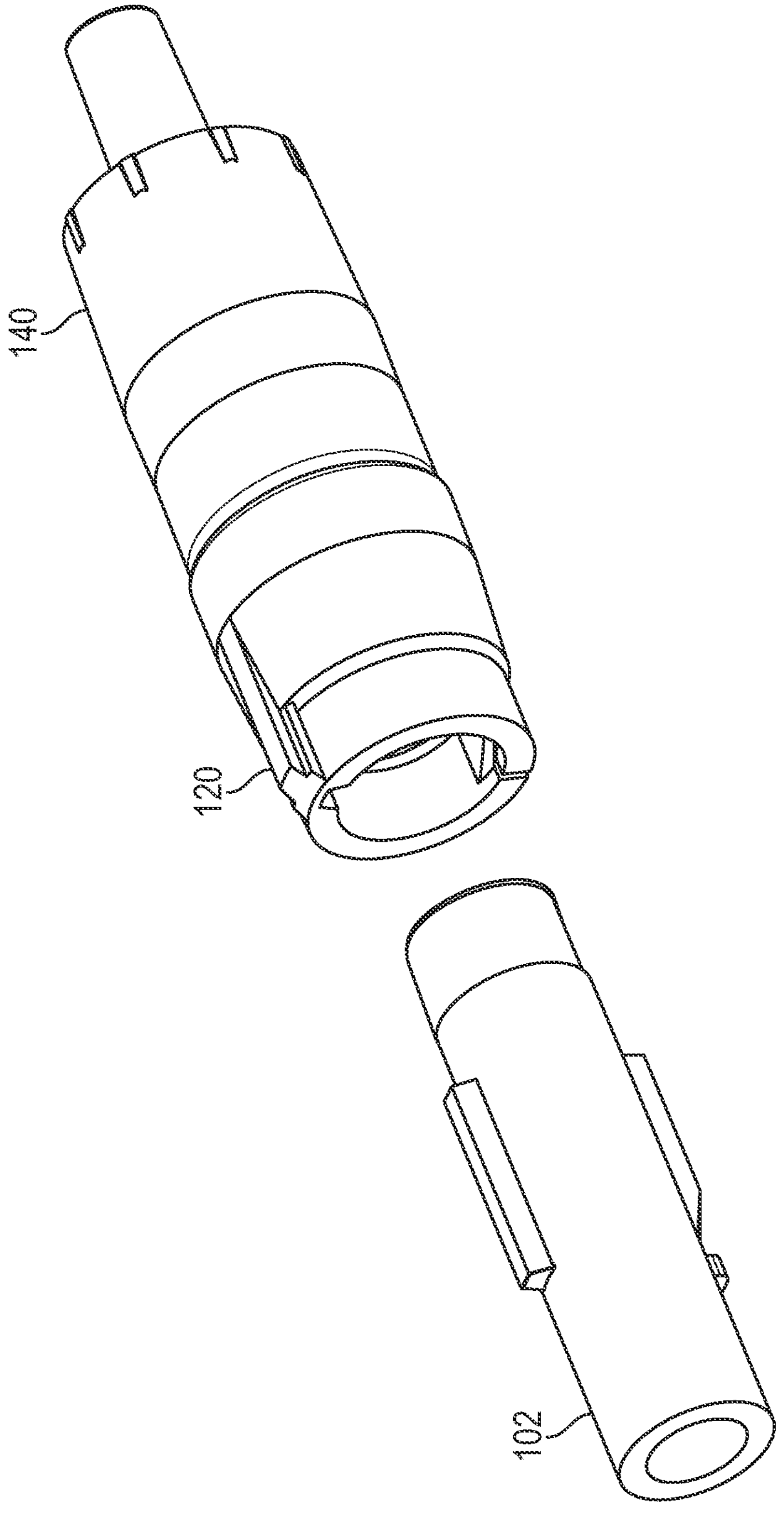
FIG. 5C is a side perspective view of the coupler assembly of FIG. 5A.
Figure 5D:
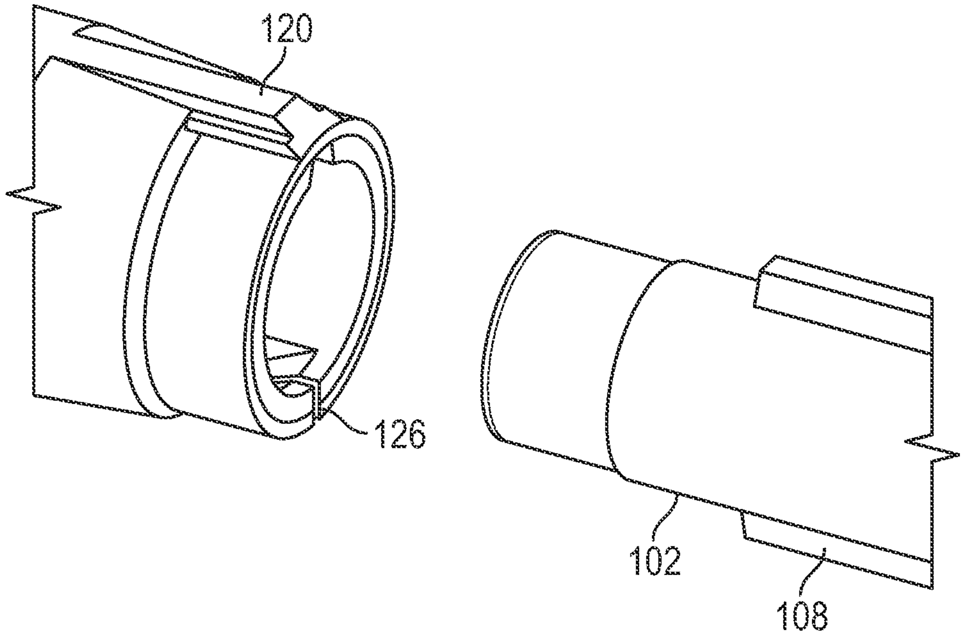
FIG. 5D is a zoomed in perspective view of the coupler assembly of FIG. 5A.
Figure 6:
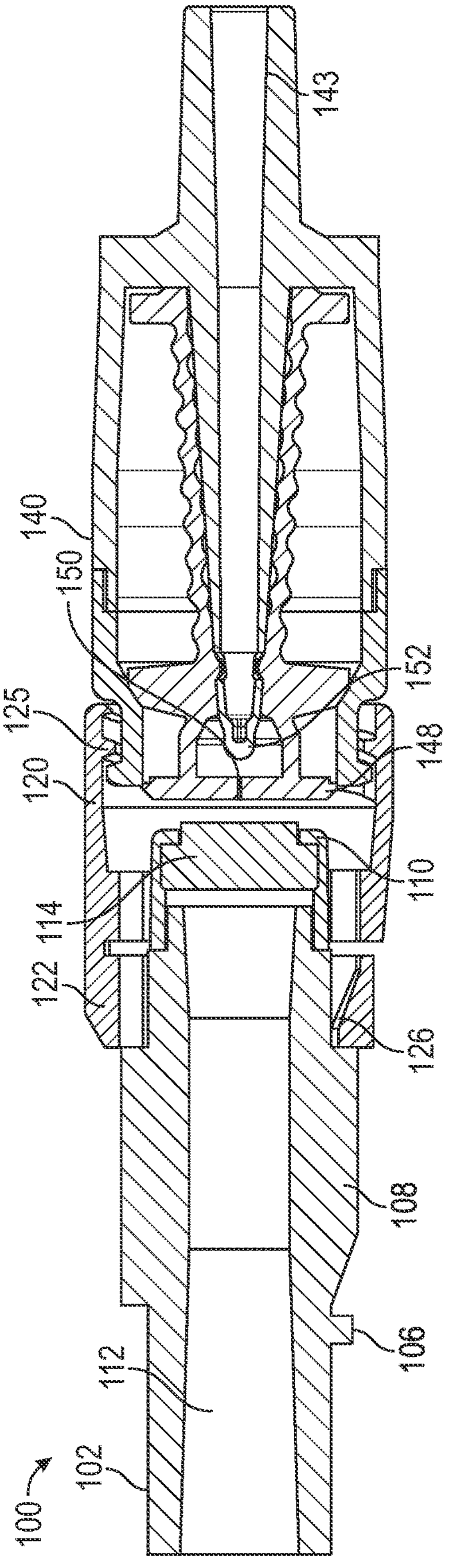
FIG. 6 is a cross-sectional side view of the coupler assembly of FIG. 1A, in accordance with some embodiments of the present disclosure.

FIG. 5A is side view of the coupler assembly of FIG. 1A with the first connector decoupled from the collar and the second connector, in accordance with some embodiments of the present disclosure. FIG. 5B is a cross-sectional view of the coupler assembly of FIG. 5A across plane B-B. FIG. 5C is a side perspective view of the coupler assembly of FIG. 5A. FIG. 5D is a zoomed in perspective view of the coupler assembly of FIG. 5A. FIG. 6 is a cross-sectional side view of the coupler assembly of FIG. 1A, in accordance with some embodiments of the present disclosure.

Referring to FIGS. 4A-5, first connector 102 is configured to decouple from collar 120 and second connector 140. In some embodiments, first connector 102 is secured to second connector 140 via collar 120 and first connector 102 is configured to decouple from collar 120. In some embodiments, first connector 102 is configured to decouple from collar 120 due to a disconnection event, which is caused by a pullout force. For example, a pullout force (e.g., force F) may be applied to first connector 102, either by being directly applied to first connector 102 or indirectly applied to first connector 102, such as being applied to tubing coupled to first connector 102. The pullout force may cause first connector 102 to move axially away from collar 120 and second connector 140 along central axis A-A thereby decoupling first connector 102 from collar 120 and second connector 140.

In some embodiments, first connector 102 is decoupled from collar 120 and thus second connector 140 when force F exceeds a predetermined threshold force. For example, if force F is less than the predetermined threshold force, first connector 102 may not decouple from collar 120 and second connector 140. The predetermined threshold force prevents inadvertent or accidental decoupling based on minor forces or movements. The predetermined threshold force may be based on ring 122 and slot 126. For example, ring 122 being substantially stiff may result in slot 126 requiring significant force to move from the closed position to the open position. In some embodiments, the predetermined threshold force is approximately 4 pounds (lbs). The predetermined threshold force may be from approximately 1 lb to approximately 8 lbs, approximately 3 lbs to approximately 7 lbs, approximately 4 lbs to approximately 6 lbs, or greater than 8 lbs. For example, a patient may have a needle/catheter inserted into their skin and the needle/catheter may be coupled to first connector 102 or second connector 140. The patient may walk away from an infusion pump or accidental pull on a fluid line coupled to first connector 102 or second connector 140 and the force exceeds 4 lbs, first connector 102 may automatically release or decouple from collar 120, effectively closing the fluid pathway between first connector 102 and second connector 140, as described herein.

When first connector 102 decouples from collar 120 due to the disconnection event, collar 120 may remain secured and coupled to second connector 140. In some embodiments coupler assembly 100 is configured to be in a third configuration where first connector 102 is decoupled from collar 120 and collar 120 is secured and coupled to second connector 140. For example, first connector 102 may be decoupled from collar 120 and second connector 140 resulting in collar 120 remaining secured to second connector 140. First connector 102 being decoupled from collar 120 and second connector 140 results in first connector 102 being spaced apart from collar 120 and second connector 140.

First connector 102 may decouple from collar 120 in response to force F exceeding a predetermined threshold force. When force F exceeds the predetermined threshold force, ramp 109 of wedge 108 exerts a force on inclined surface 128, which may cause radial deflection of ring 122 (e.g., first ring portion **122*a* and second ring portion 122*b*). Radial deflection of ring 122 allows wedge 108 to be removed from slot 126 in response to force F, thereby allowing first connector 102 to axially move away from collar 120 and second connector 140 and decoupling first connector 102 from collar 120**.

In some embodiments, when first connector 102 is decoupled from collar 120 and second connector 140, slot 126 moves to the closed position due to ring 122 (e.g., first ring portion **122*a* and second ring portion 122*b*) being biased radially inwards. When slot 126 is in the closed position, first connector 102 is prevent from being coupled to second connector 140. For example, wedge 108 may be prevented from being inserted into or disposed through slot 126 since slot 126 moves to the closed position upon decoupling of first connector 102 from collar 120. Preventing wedge 108 from being inserted into or disposed through slot 126 prevents first connector 102 from coupling with second connector 140. For example, preventing wedge 108 from being inserted into or disposed through slot 126 may result in only second end 103 being partially disposed within collar 120 but preventing second end 103 from contacting, abutting, or coupling to second connector 140**.

In some embodiments, collar 120 does not include slot 126. Collar 120 may be configured to couple to first connector 102 (e.g., via wedge 108) and prevent first connector 102 from decoupling when force F is less than the predetermined threshold force. For example, collar 120 may include a compressible material that abuts wedge 108 when wedge 108 is disposed within collar 120. The compressible material may be configured exert a compression force on wedge 108, thereby securing wedge 108 in place and to collar 120. In response to force F exceeding the predetermined threshold force, the compressible material may be configured to compress allowing wedge 108 to slide through collar 120 and allowing first connector 102 to decouple from collar 120. The compressible material may increase in size after first connector 102 is decoupled thereby blocking the access of wedge 108 into collar 120 and preventing first connector 102 from coupling with collar 120.

Referring to FIG. 6, preventing first connector 102 from re-coupling with second connector 140 by preventing wedge 108 from being disposed within slot 126 when slot 126 is in the closed position results in pin 152 and/or valve 148 no longer contact first connector 102 (e.g., valve 114). This prevents contamination of valve 148, pin 152, and/or other components of second connector 140 by first connector 102 (e.g., valve 114). For example, first connector 102 may be decoupled from second connector 140 and collar 120 based on a disconnection event (e.g., force F exceeding the predetermined threshold force). The disconnection event may cause first connector 102 to fall to the floor, contact another surface or patient, or otherwise be exposed to unclean or unsterile environments. Allowing recoupling of first connector 102 to second connector 140 after a disconnection event may result in contaminants (e.g., bacteria, debris, viruses, etc.) entering the fluid pathway between first connector 102 and second connector 140, which may cause infection to the user (e.g., the patient). Allowing recoupling of first connector 102 to second connector 140 after a disconnection event may result in contaminants entering the bloodstream or other exposed areas of the patient resulting in sepsis.

Figure 7:
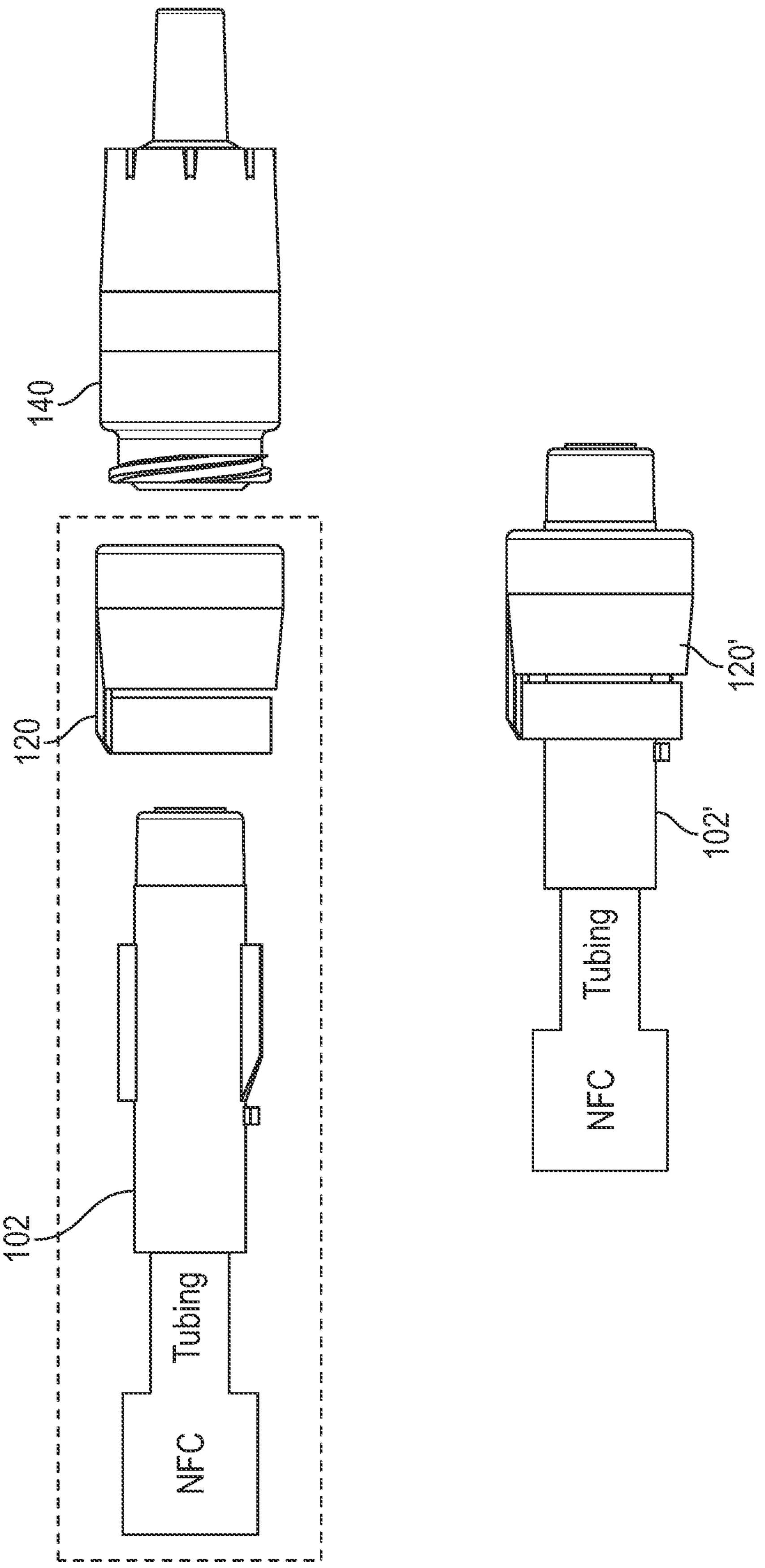
FIG. 7 is side view of the coupler assembly of FIG. 1A and a replacement coupler assembly, in accordance with some embodiments of the present disclosure.

FIG. 7 is side view of the coupler assembly of FIG. 1A and a replacement coupler assembly, in accordance with some embodiments of the present disclosure.

Referring to FIG. 7, upon a disconnection event, first connector 102 is prevented from being recoupled to second connector 140 and is prevented from being secured to collar 120, such as via wedge 108 being prevented from being inserted into slot 126. After the disconnection event, collar 120 may be disconnected from second connector 140, and first connector 102 and collar 120 may be discarded. Further, after the disconnection event the flow of fluid within second connector 140 may stop or be reduced to prevent leakage or spillage of the fluid. A sterile first connector 102' and a sterile collar 120' may be retrieved to couple to second connector 140. In some embodiments, first connector 102' is coupled to collar 120' similar to when coupler assembly 100 is in the first configuration. First connector 102' and collar 120' may be coupled to second connector 140 and the flow of fluid through second connector 140 may resume to allow the flow of fluid to pass through second connector 140, collar 120', and first connector 102'.

Figure 8A:
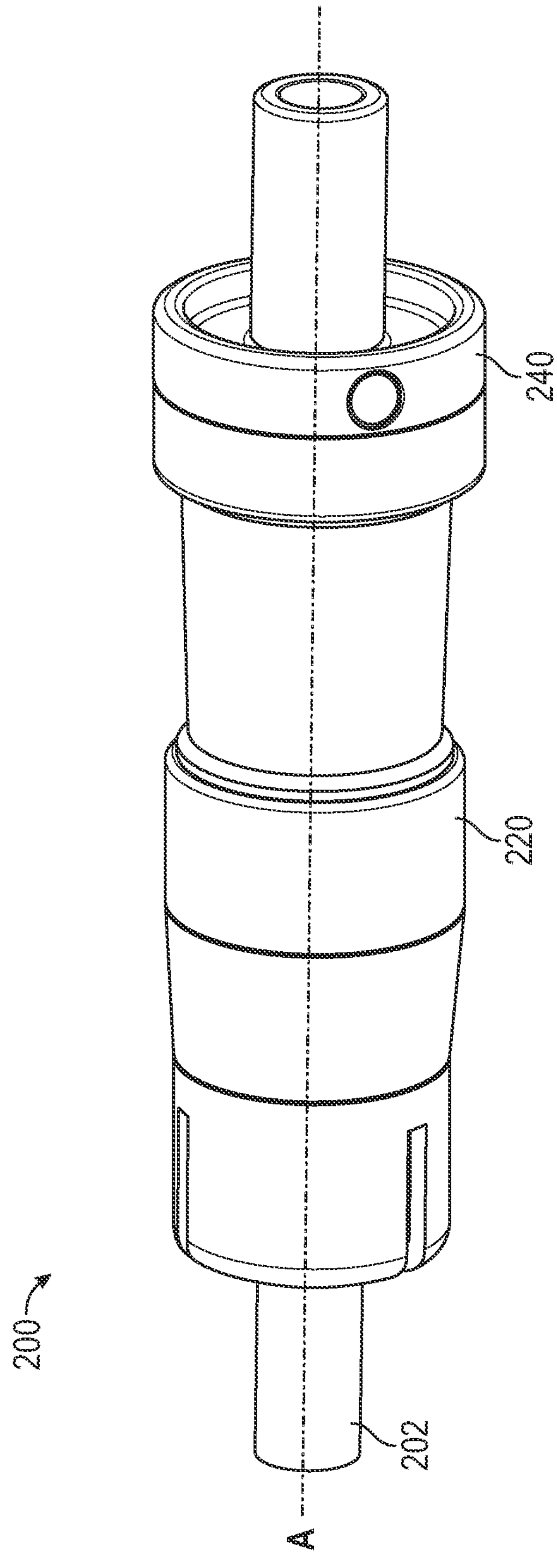
FIG. 8A is a side view of a coupler assembly, in accordance with various aspects of the present disclosure.
Figure 8B:
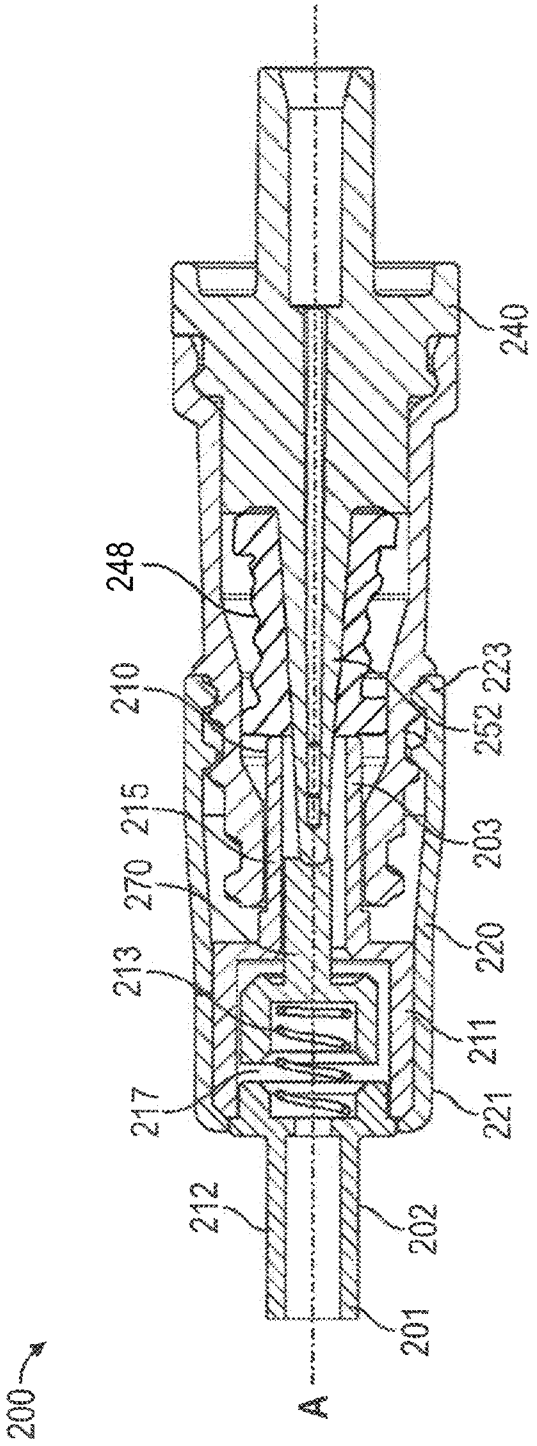
FIG. 8B is a cross sectional side view of the coupler assembly of FIG. 8A.
Figure 9:
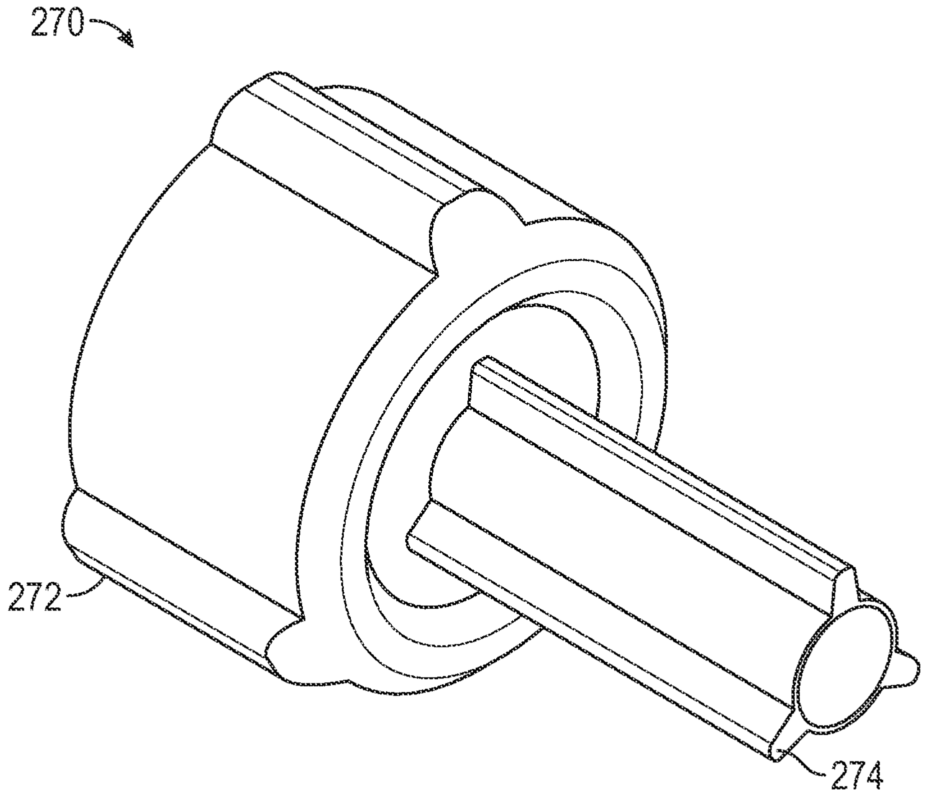
FIG. 9 is a side perspective view of a valve of the coupler assembly of FIG. 8A.

FIG. 8A is a side view of a coupler assembly, in accordance with various aspects of the present disclosure. FIG. 8B is a cross sectional side view of the coupler assembly of FIG. 8A. FIG. 9 is a side perspective view of a valve of the coupler assembly of FIG. 8A.

With reference to FIGS. 8A-9, coupler assembly 200 may be substantially similar to coupler assembly 100. For example, coupler assembly 200 may allow for the flow of fluid from a fluid source to a patient. Coupler assembly 200 may include first connector 202, collar 220, and second connector 240. Coupler assembly 200, similar to coupler assembly 100, may prevent flow of fluid through coupler assembly 200 in response to a disconnection event.

Collar 220 may be configured to couple first connector 202 to second connector 240. In some embodiments, coupler assembly 200 includes central axis A-A and first connector 202, collar 220, and second connector 240 are coupled in series along central axis A-A. First connector 202 and/or second connector 240 may allow for the connection and/or disconnection of tubing to allow for selective fluid communication therebetween. Central axis A-A may extend longitudinally along the length of first connector 202, collar 220, and second connector 240. First connector 202 may be similar to first connector 102, collar 220 may be similar to collar 120, and second connector 140 may be similar to second connector 240.

Similar to the operation of coupler assembly 100, coupler assembly 200 has first configuration, a second configuration, and third configuration. In the first configuration, collar 220 is coupled to first connector 202 and first connector 202 and collar 220 are decoupled from second connector 240. In some embodiments, coupler assembly 200 is shipped in the first configuration. In the second configuration, first connector 202 is coupled to collar 220, and collar 220 is coupled to second connector 240 such that a portion of second connector 240 (e.g., pin 252) is disposed within first connector 202 to allow fluid communication between first connector 202 and second connector 240 through collar 220. In some embodiments, similar to coupler assembly 100, a disconnection event occurs resulting in first connector 202 decoupling from collar 220, while collar 220 remains coupled to second connector 240. In the third configuration, first connector 202 is decoupled from collar 220 and collar 220 remains coupled to second connector 240. In some embodiments, coupler assembly 200 transitions from the second configuration to the third configuration in response to a disconnection event.

In the second configuration (FIG. 8B), collar 220 couples first connector 202 to second connector 240 such that first connector 202 is in fluid communication with second connector 240. First connector 202 may first end 201 and second end 203 disposed opposite first end 201. In some embodiments, first connector 202 includes tubing portion 212, body 211, and conduit 215. Body 211 may be disposed between tubing portion 212 and conduit 215. In some embodiments, body 211 includes interior space 217. Body 211 may include biasing member 213 and valve 270. Biasing member 213 may be disposed within interior space 217 and be coupled to tubing portion 212. In some embodiments, biasing member 213 is a spring. Biasing member 213 may be coupled to tubing portion 212 at one end and valve 270 at the other end. Valve 270 (FIG. 9) may be disposed within interior space 217 and include body 272 and extending member 274. Extending member 274 may extend outwardly from body 272. In some embodiments, body 272 of valve 270 is disposed within interior space 217 and extending member 274 at least partially extends into conduit 215.

Valve 270 may have an open configuration and a closed configuration. In the open configuration, body 272 of valve 270 is disposed proximate first end 201 compared to when valve 270 is in the closed configuration. In the open configuration, biasing member 213 is in a contracted stated such that valve 270 is proximate tubing portion 212 compared to when valve 270 is in the closed configuration. Valve 270 being in the open configuration allows fluid to flow from second connector 240, through conduit 215 into interior space 217 and through tubing portion 212. In some embodiments, when valve 270 is in the open configuration, extending member 274 is at least partially disposed within interior space 217. In some embodiments, valve 270 is in the open configuration due to pin 252 contacting and pushing valve 270, causing biasing member 213 to be in the contracted state. For example, when collar 220 couples first connector 202 and second connector 204, pin 252 of second connector 240 is at least partially disposed within conduit 215 causing pin 252 to abut and push against valve 270 to cause valve 270 to be in the open position and allow a fluid pathway to form between second connector 240 and first connector 202. When pin 252 is not pushing and/or abutting valve 270 (e.g., when coupler assembly 100 is not in the second configuration), biasing member 213 is biased to be in the extend state resulting in valve 270 being in the closed configuration and preventing fluid form flowing from conduit 215 to interior space 217.

As discussed in further detail below, in the closed configuration, body 272 of valve 270 is disposed proximate second end 203 compared to when valve 270 is in the open configuration. In the closed configuration, body 272 abuts an opening of conduit 215 preventing fluid from flowing from conduit 215 into interior space 217. In some embodiments, when valve 270 is in the closed configuration, biasing member 213 is in an extended state resulting in valve 270 being pushed against conduit 215 and sealing conduit 215.

Figure 10A:
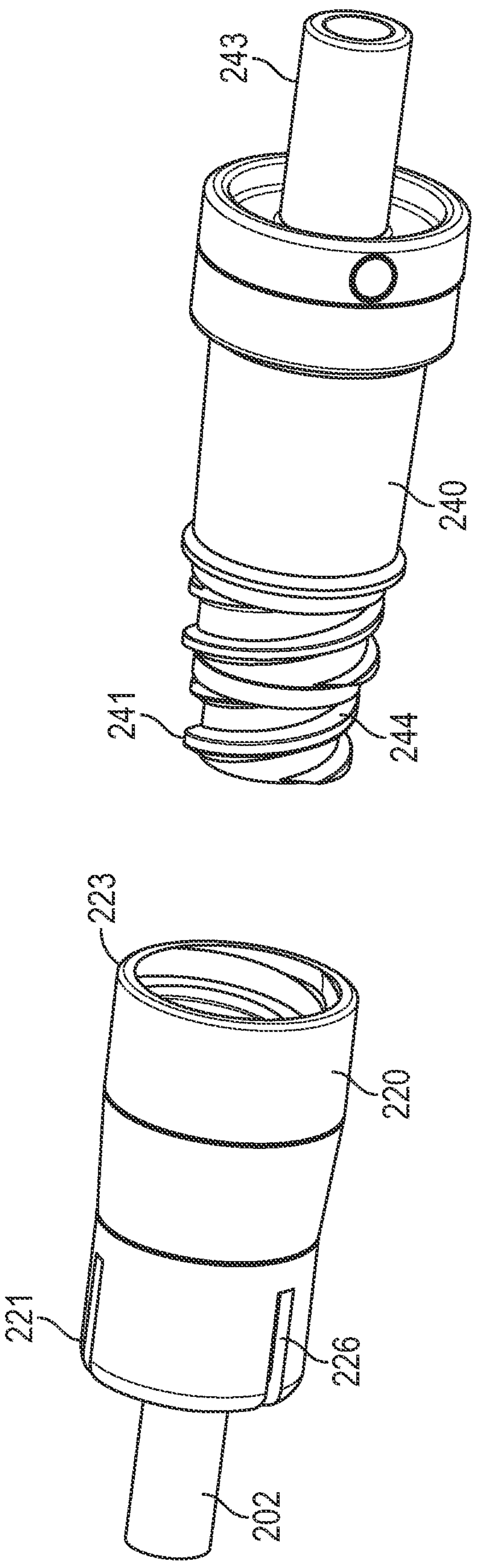
FIG. 10A is a side perspective view of the coupler assembly of FIG. 8A with a collar coupled to a first connector and disconnected from a second connector, in accordance with some embodiments of the present disclosure.
Figure 10B:
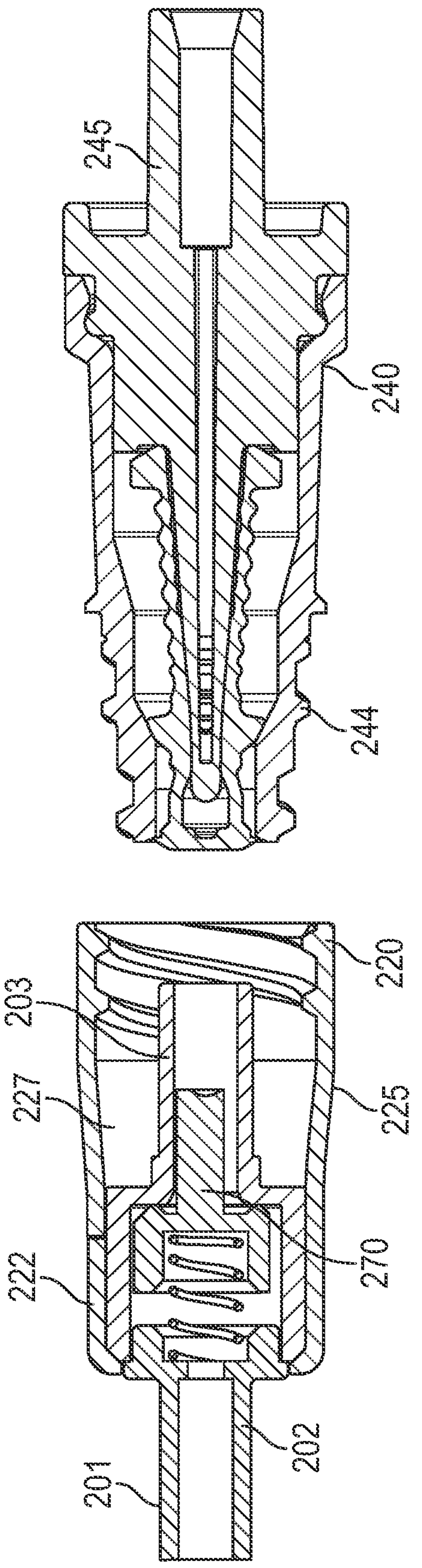
FIG. 10B is a cross sectional side view of the coupler assembly of FIG. 10A.

FIG. 10A is a side perspective view of the coupler assembly of FIG. 8A with a collar coupled to a first connector and disconnected from a second connector, in accordance with some embodiments of the present disclosure. FIG. 10B is a cross sectional side view of the coupler assembly of FIG. 10A.

With reference to FIGS. 10A and 10B, similar to coupler assembly 100, coupler assembly 200 may have a first configuration where first connector 202 is coupled to collar 220, and first connector 202 and collar 220 are not connector or are decoupled from second connector 240. In some embodiments, coupler assembly 200 is shipped in the first configuration to prevent damage to valves of coupler assembly 200. In some embodiments, collar 220 includes releasing portion 222 and body 225. Releasing portion 222 may be disposed opposite body 225. In some embodiments, releasing portion 222 and body 225 form a unitary structure (e.g., collar 220). In alternative embodiments, releasing portion 222 is coupled to body 225.

Releasing portion 222 may be coupled to body 211 to secure collar 220 to first connector 202. In some embodiments, when collar 220 is coupled to first connector 202, body 211 and conduit 215 are disposed within collar 220. Releasing portion 222 may circumferentially surround at least body 211 to secure first connector 202 to collar 220. In some embodiments, first connector 202 is secured within and to collar 220 via friction fitting at least a portion of first connector 202 (e.g., body 211) into collar 220. For example, releasing portion 222 may include one or more slots 226 configured to allow releasing portion 222 to radially expand to receive first connector 202. In some embodiments, releasing portion 222 is biased radially inward and includes one or more slots 226 to allow releasing portion 222 to expand radially outward to receive and secure first connector 202.

Releasing portion 222 having one or more slots 226 allows collar 220 to be releasably coupled to first connector 202. For example, when collar 220 is coupled to first connector 202, releasing portion 222 circumferentially surround first connector 202 and prevents decoupling (e.g., due to friction fitting) unless force F has been exceeded (e.g., a pullout force exceeding a predetermined threshold). Slots 226 may be circumferentially disposed around releasing portion 222. In some embodiments, slots 226 extend at least partially along the length of collar 220. Collar 220 may include first end 221 and second end 223 disposed opposite first end 221. Slots 226 may extend longitudinally from first end 221 to a portion of body 225. In some embodiments, slots 226 longitudinally extend at least partially along collar 220 such that each slot 226 is parallel to central axis A-A.

Coupler assembly 200 may transition from the first configuration (FIG. 10A) to the second configuration (FIG. 8A) by coupling collar 220 to second connector 240. For example, similar to second connector 140, second connector 240 may include mating portion 244 and connecting portion 245 disposed opposite mating portion 244. Collar 220 may couple to mating portion 244 and connecting portion 245 may be coupled to a portion of tubing. In some embodiments, an interior surface of collar 220 at least partially includes threads configured to engage with mating portion 244. For example, an interior surface of collar 220 may include threads configured to engage with threads of mating portion 244 to threadably couple collar 220 to second connector 240. In some embodiments, collar 220 includes a first set of threads disposed on an interior surface proximate second end 223 and mating portion 244 includes a second set of threads configured to threadably engage with the first set of threads to secure mating portion 244 and second connector 240 to collar 220.

In the second configuration, pin 252 pushes against valve 270 to cause valve 270 to be in the open configuration. Second connector 240 may include first end 241 and second end 243 disposed opposite first end 241. In the second configuration, first end 241 of second connector 240 may be disposed within second end 203 of first connector 202. This causes valve 248 of second connector 240 and valve 270 of first connector 202 to both be in the open configuration and form a fluid pathway between first connector 202 and second connector 240.

In some embodiments, when coupler assembly 200 is in the second configuration, valve 270 is in the closed configuration. Valve 270 may be in the closed configuration due to biasing element 213 being biased to be in the extended state. Valve 270 being in the closed configuration results in conduit 215 not being in fluid communication with interior space 227. Due to coupler assembly 200 being shipped in the second configuration, valve 270 may remain in the closed configuration to prevent debris or other particulates from entering into first connector 202.

Figure 11A:
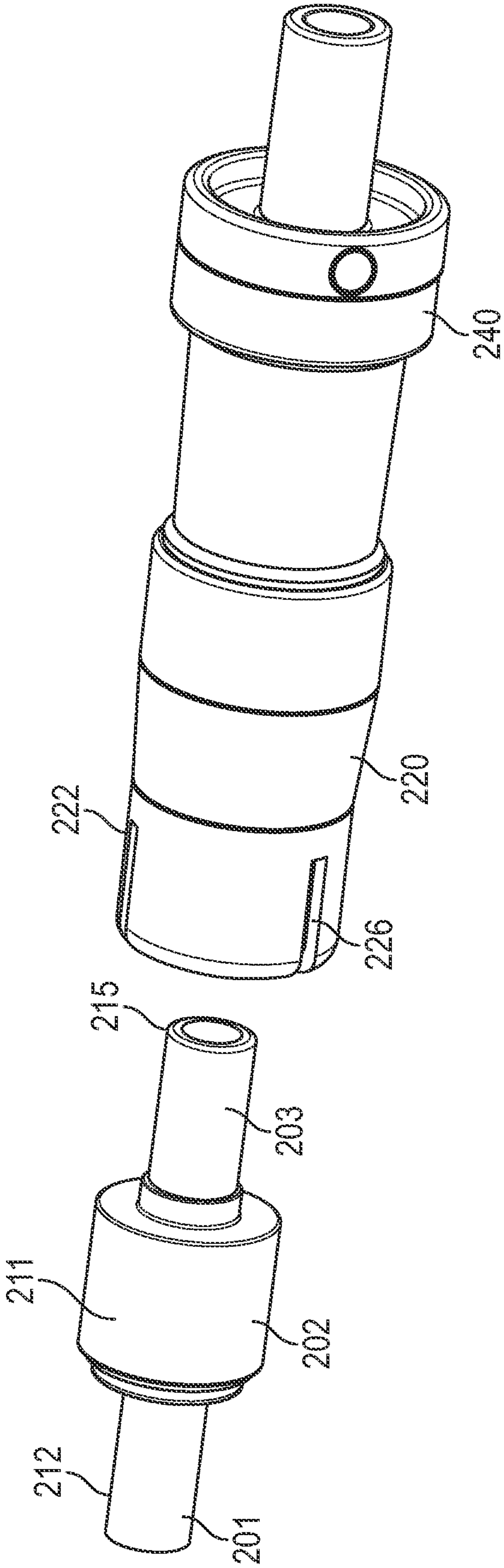
FIG. 11A is a side perspective view of the coupler assembly of FIG. 8A with the first connector decoupled from the collar and the second connector, in accordance with some embodiments of the present disclosure.
Figure 11B:
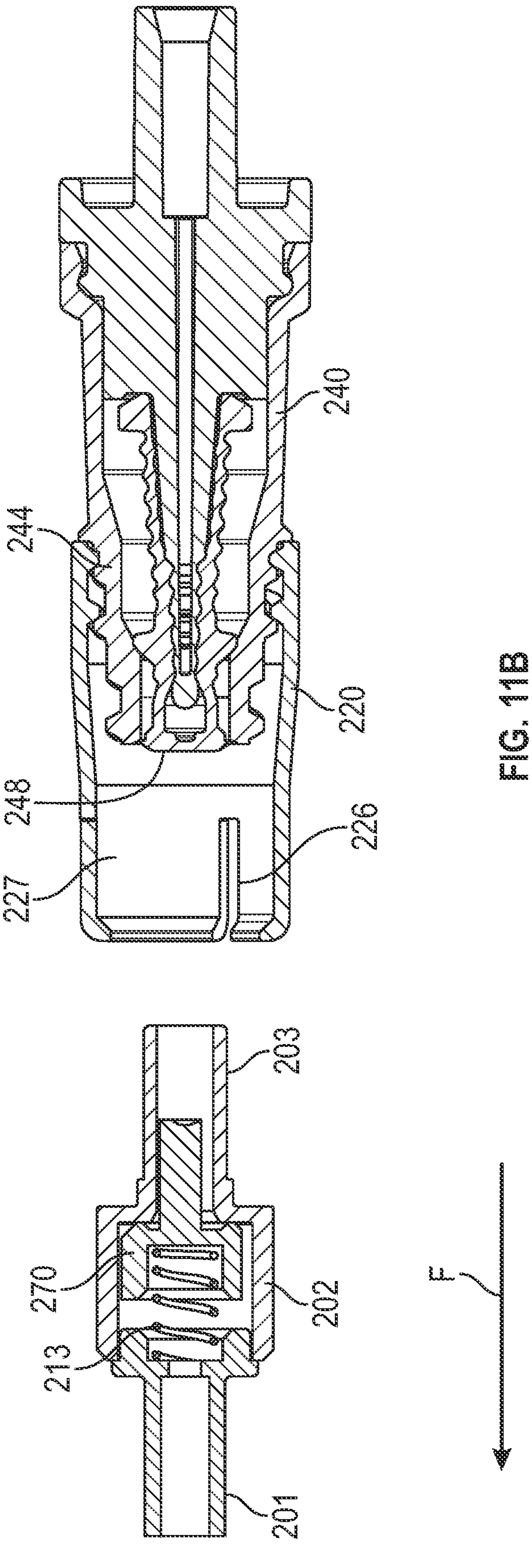
FIG. 11B is a cross sectional side view of the coupler assembly of FIG. 11A.

FIG. 11A is a side perspective view of the coupler assembly of FIG. 8A with the first connector decoupled from the collar and the second connector, in accordance with some embodiments of the present disclosure. FIG. 11B is a cross sectional side view of the coupler assembly of FIG. 11A.

With reference to FIGS. 11A-11B, coupler assembly 200 may be configured to be in the third configuration. Coupler assembly 200 may transition from the second configuration to the third configuration in response to a disconnection event (e.g., a pullout force exceeding a predetermined threshold). Upon the pullout force exceeding a predetermine threshold, similar to coupler assembly 100, first connector 202 may decouple from collar 220, which is coupled (e.g., threadably engaged) to second connector 240. First connector 202 may decouple due to the pullout force F exceeding the predetermined threshold, which overcome the frictional force between releasing portion 222 and first connector 202. Due to collar 220 being threadably coupled to second connector 240, the pullout force exceeding the predetermined threshold does not result in collar 220 decoupling from second connector 240.

When couple assembly 200 is in the first configuration (FIG. 8A), collar 220 is threadably engaged to second connector 240 (e.g., mating portion 244). Collar 220 being threadably engaged to second connector 240 prevents collar 220 from decoupling from second connector 240 in response to a disconnection event (e.g., a pullout force exceeding a predetermined threshold). In some embodiments, in response to a disconnection event, first connector 202 decouples from releasing portion 222 and collar 220 while collar 220 remains threadably coupled to second connector 240, thereby transitioning coupler assembly 200 from the second configuration (FIG. 8A) to the third configuration (FIG. 11A).

In some embodiments, second connector 240 includes valve 248. Valve 248 may be similar to valve 148 and may be configured to control the flow of fluid. For example, second connector 240 may be coupled to a second portion of tubing and may include valve 248 that is configured to control the flow of fluid to or from the second portion of tubing to first connector 202 when coupled to second connector 240. In some embodiments, valve 248 has an open configuration and closed configuration. In the open configuration, valve 248 may be configured to allow fluid to flow through second connector 240. In the closed configuration, valve 148 may be configured to block or prevent the flow of fluid through second connector 240. In some embodiments, valve 248 is in the open configuration when first connector 202 is coupled to second connector 240 via collar 220. Valve 248 may be in the closed position upon disconnecting or decoupling of first connector 202 from second connector 240 and/or collar 220 (e.g., when coupler assembly is in the first configuration or the third configuration).

Figure 12A:
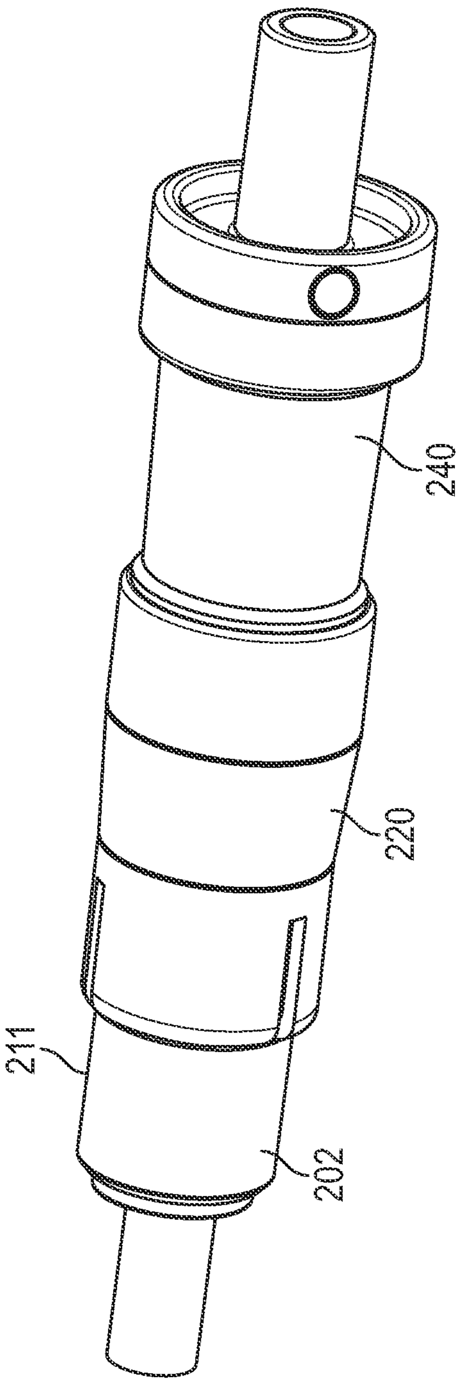
FIG. 12A is a side perspective view of the coupler assembly of FIG. 8A with the first connector recoupled to the collar after being detached from the collar and the second connector, in accordance with some embodiments of the present disclosure.
Figure 12B:
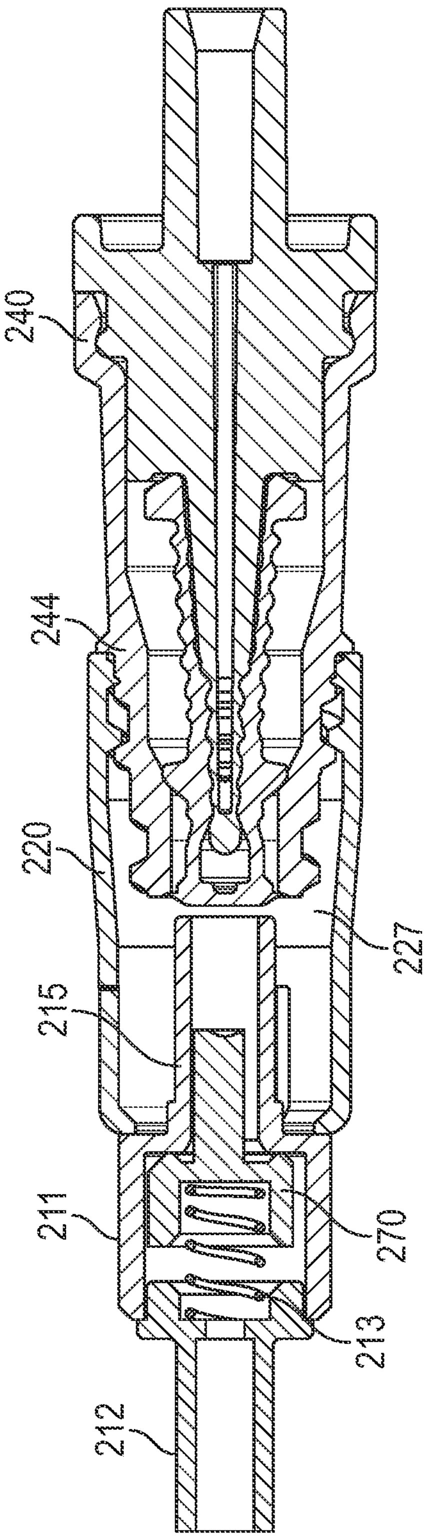
FIG. 12B is a cross sectional side view of the coupler assembly of FIG. 12A.

FIG. 12A is a side perspective view of the coupler assembly of FIG. 8A with the first connector recoupled to the collar after being detached from the collar and the second connector, in accordance with some embodiments of the present disclosure. FIG. 12B is a cross sectional side view of the coupler assembly of FIG. 12A.

With reference to FIGS. 12A-12B, similar to coupler assembly 100, once first connector 202 is decoupled from collar 220, first connector 202 may be prevented from recoupling to collar 220, which is coupled to second connector 240. For example, once first connector 202 is decoupled from releasing portion 222, releasing portion 222 may flex radially inward and prevent first connector 202 from recoupling to collar 220. This prevents first connector 202 from being recoupled to collar 220 and second connector 240 after a disconnection event. This prevents contamination of valve 248, pin 252, and/or other components of second connector 240 by first connector 202 after a disconnection event. For example, first connector 202 may be decoupled from second connector 240 and collar 220 based on a disconnection event (e.g., force F exceeding the predetermined threshold force). The disconnection event may cause first connector 202 to fall to the floor, contact another surface or patient, or otherwise be exposed to unclean or unsterile environments. Allowing recoupling of first connector 202 to second connector 240 via collar 220 after a disconnection event may result in contaminants (e.g., bacteria, debris, viruses, etc.) entering the fluid pathway between first connector 202 and second connector 240, which may cause infection to the user (e.g., the patient). Allowing recoupling of first connector 202 to second connector 240 after a disconnection event may result in contaminants entering the bloodstream or other exposed areas of the patient resulting in sepsis.

Similar to coupler assembly 100, after the disconnection event, collar 220 may be disconnected from second connector 140 by threadably disengaging collar 220 from second connector 240, and first connector 202 and collar 220 may be discarded. Further, after the disconnection event the flow of fluid within second connector 240 may stop or be reduced to prevent leakage or spillage of the fluid.

The disclosures described here including at least the following clauses:

Clause 1: A coupler comprising a first connector having a first end, a second end opposite the first end, and a first valve disposed between the first end and the second end, a second connector having a mating portion, a connecting portion opposite the mating portion, and a second valve disposed at least partially within the mating portion, and a collar having a body detachably coupled to the mating portion of the second connector and a releasing portion disposed opposite the body, the releasing portion configured to receive at least a portion of the first connector to detachably couple the first connector to the collar and the second connector such that the first end of the first connector is disposed within the second connector. The first connector is configured to decouple from the collar and the second connector and is prevented from re-coupling to the collar once decoupled.

Clause 2: The coupler of clause 1, wherein the first connector is configured to decouple from the collar in response to a pullout force exceeding a predetermined threshold force.

Clause 3: The coupler of clause 2, wherein the pullout force is a force applied to the first connector along a central axis of the first connector.

Clause 4: The coupler of claim 3, wherein the central axis extends at least along a length of the first connector.

Clause 5: The coupler of clause 3, wherein the central axis extends through the first connector, the collar, and the second connector when the first connector is coupled to the collar and the collar is coupled to the second connector.

Clause 6: The coupler of clause 2, wherein the first connector is configured to remain coupled to the collar when the pullout force does not exceed the predetermined threshold force.

Clause 7: The coupler of clause 1, wherein the ring has a slot longitudinally extending through the ring.

Clause 8: The coupler of clause 7, wherein the slot is configured to allow the releasing portion to radially expand outwards.

Clause 9: The coupler of clause 8, wherein upon decoupling of the first connector from the collar, the slot allows the releasing portion to flex radially inwards.

Clause 10: The coupler of clause 8, wherein the first valve is prevented from contacting the second valve when the slot is flexed radially inwards.

Clause 11: The coupler of clause 8, wherein the first connector includes a body having an interior space, the interior space housing the first valve.

Clause 12: The coupler of clause 11, wherein the first connector includes a biasing element disposed within the interior space, the biasing element coupled to the first valve.

Clause 13: The coupler of clause 1, wherein the first connector includes a guide and the collar includes a channel sized and shaped to receive the guide to prevent rotational movement of the first connector relative to the collar when the guide is disposed within the channel.

Clause 14: The coupler of clause 13, wherein the guide extends from an external surface of the first connector and the first connector includes a wedge extending from the external surface opposite the guide, the wedge sized and shaped to be received by a slot disposed on the collar.

Clause 15: The coupler of clause 1, wherein the collar includes a ring, and the ring includes a slot longitudinally extending through the collar.

Clause 16: The coupler of clause 15, wherein the ring includes a first ring portion and a second ring portion, and the slot is disposed between the first ring portion and the second ring portion.

Clause 17: The coupler of clause 15, wherein the collar includes a body coupled to the ring via a channel, the body being disposed proximate the connecting portion of the second connector and the ring being disposed proximate the first end of the first connector when the first connector and the second connector are coupled to the collar.

Clause 18: The coupler of clause 1, wherein the first valve is disposed proximate the second valve when the first connector is coupled to the collar.

Clause 19: The coupler of clause 1, wherein the second end of the first connector is disposed within the second connector when the first connector is coupled to the collar.

Clause 20: The coupler of clause 1, wherein the second end of the first connector is disposed within the mating portion of the second connector when the first connector is coupled to the collar.

Clause 21: The coupler of clause 1, wherein the first connector includes a wedge having a ramp and the collar includes a slot sized and shaped to receive the wedge such that the wedge is at least partially disposed within the slot when the first connector is coupled to the collar.

Clause 22: The coupler of clause 1, wherein the first connector includes a stopper configured to prevent axially movement of the collar to an area proximate the first end.

Clause 23: The coupler of clause 1, wherein the second end of the first connector has a maximum diameter less than a maximum diameter of the mating portion of the second connector.

Clause 24: The coupler of clause 1, wherein the coupler has a first configuration and in the first configuration the first connector is disposed within the collar such that the collar is disposed between the first end and the second end.

Clause 25: The coupler of clause 1, wherein the coupler has a second configuration and in the second configuration the first connector is coupled to the collar and the collar is coupled to the second connector.

Clause 26: The coupler of clause 1, wherein the coupler has a third configuration and in the third configuration the first connector is disconnected from the collar and the collar is coupled to the second connector.

Clause 27: The coupler of clause 1, wherein the first connector is coupled to a first portion of tubing at the first end and the second connector is coupled to a second portion of tubing at the connecting portion.

Clause 28: The coupler of clause 1, wherein the mating portion has a maximum diameter greater than a maximum diameter of the connecting portion.

Clause 29: The coupler of clause 1, wherein the first end has a maximum diameter substantially the same as a maximum diameter of the second end.

Clause 30: The coupler of clause 1, wherein the second connector includes a pin disposed between the mating portion and the connecting portion, and the pin at least partially extends into the first valve when the first connector is coupled to the collar and the collar is coupled to second connector.

Clause 31: The coupler of clause 1, wherein a fluid pathway is formed between the connecting portion of the second connector and the first end of the first connector when the first connector is coupled to the collar and the collar is coupled to the second connector.

Clause 32: A coupler comprising a first connector having a first end, a second end opposite the first end, a central axis extending through at least the first end and the second end, a body disposed between the first end and the second end, and a first valve disposed proximate the second end, a second connector having a threaded mating portion, a connecting portion opposite the mating portion, a second valve disposed within the mating portion, and pin disposed at least partially within the mating portion, and a collar having a releasing portion detachably coupled to the first connector and a body detachably coupled to the mating portion of the second connector. The collar is configured to couple the first connector to the second connector such that at least the first end of the first connector is disposed within the second connector. The first connector is configured to decouple from the collar and the second connector in response to a pullout force exceeding a predetermined threshold force. The first connector is prevented from re-coupling to the second connector and the collar once decoupled.

Clause 33: A coupler comprising a first connector having a first end, a second end opposite the first end, a central axis extending through at least the first end and the second end, a body disposed between the first end and the second end, and a first valve disposed proximate the second end, the body having an interior space housing the first valve and a biasing element coupled to the first valve, a second connector having a threaded mating portion, a connecting portion opposite the mating portion, a second valve disposed within the mating portion, and pin disposed at least partially within the mating portion, and a collar having a releasing portion detachably coupled to the first connector and a body threadably coupled to the mating portion of the second connector, the releasing portion having a slot longitudinally extending through the releasing portion, the slot being configured to allow the releasing portion to expand radially outward to detachably couple the first connector to the releasing portion of the collar. The collar is configured to couple the first connector to the second connector such that at least the first end of the first connector is disposed within the second connector. The first connector is configured to decouple from the collar and the second connector in response to a pullout force exceeding a predetermined threshold force. The first connector is prevented from re-coupling to the second connector and the collar once decoupled. The central axis extends through the first connector, the collar and the second connector when the collar is coupled to the first connector and the second connector.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A coupler comprising:

a first connector having a first end, a second end opposite the first end, a central axis extending through at least the first end and the second end, a body disposed between the first end and the second end, and a first valve disposed proximate the second end;

a second connector having a threaded mating portion, a connecting portion opposite the mating portion, a second valve disposed within the mating portion, and a pin disposed at least partially within the mating portion; and a collar having:

- a releasing portion detachably coupled to the first connector and comprising a first portion, a second portion, and a slot disposed therebetween, the first and second portions being separated by the first connector when the releasing portion is coupled to the first connector; and
- a body detachably coupled to the mating portion of the second connector, wherein the collar is configured to couple the first connector to the second connector such that a portion of the first connector is disposed between the first portion and the second portion of the releasing portion and at least the second end of the first connector is disposed within the second connector, wherein the first connector is configured to decouple from the collar and the second connector in response to a pullout force exceeding a predetermined threshold force, wherein the first portion and the second portion are configured to draw together when the first connector decouples from the collar, wherein the first connector is prevented from re-coupling to the second connector and the collar when the first portion and the second portion are drawn together.

2. A coupler comprising:

a first connector having a first end, a second end opposite the first end, and a first valve disposed between the first end and the second end;

a second connector having a mating portion, a connecting portion opposite the mating portion, and a second valve disposed at least partially within the mating portion; and a collar having:

a body detachably coupled to the mating portion of the second connector; and a releasing portion disposed opposite the body, comprising a slot, and configured to flex radially inward to close the slot, wherein, when the slot is open, the slot receives at least a portion of the first connector to detachably couple the first connector to the collar and the second connector such that the second end of the first connector is disposed within the second connector, wherein the releasing portion flexes radially inward to close the slot when the first connector is decoupled from the collar and the second connector such that the first connector is prevented from re-coupling to the collar.

3. The coupler of claim 2, wherein the first connector is configured to decouple from the collar in response to a pullout force exceeding a predetermined threshold force.

4. The coupler of claim 3, wherein the pullout force is a force applied to the first connector along a central axis of the first connector.

5. The coupler of claim 4, wherein the central axis extends through the first connector, the collar, and the second connector when the first connector is coupled to the collar and the collar is coupled to the second connector.

6. The coupler of claim 3, wherein the first connector is configured to remain coupled to the collar when the pullout force does not exceed the predetermined threshold force.

7. The coupler of claim 2, wherein the slot at least partially longitudinally extends along the collar.

8. The coupler of claim 2, wherein the slot is configured to allow the releasing portion to radially expand outwards when the slot is open.

9. The coupler of claim 2, wherein the first valve is prevented from contacting the second valve when the releasing portion is flexed radially inwards.

10. The coupler of claim 2, wherein the first connector includes a body having an interior space, the interior space housing the first valve.

11. The coupler of claim 10, wherein the first connector includes a biasing element disposed within the interior space, the biasing element coupled to the first valve.

12. The coupler of claim 2, wherein the first connector includes a guide and the collar includes a channel sized and shaped to receive the guide to prevent rotational movement of the first connector relative to the collar when the guide is disposed within the channel.

13. The coupler of claim 12, wherein the guide extends from an external surface of the first connector and the first connector includes a wedge extending from the external surface opposite the guide, the wedge sized and shaped to be received by the slot.

14. The coupler of claim 2, wherein the first valve is disposed proximate the second valve when the first connector is coupled to the collar.

15. The coupler of claim 2, wherein the second end of the first connector is disposed within the body when the first connector is coupled to the collar.

16. The coupler of claim 2, wherein the first connector includes a wedge having a ramp and the slot is sized and shaped to receive the wedge such that the wedge is at least partially disposed within the slot when the first connector is coupled to the collar.

17. The coupler of claim 2, wherein the first connector includes a stopper configured to prevent axial movement of the collar to an area proximate the first end.

18. The coupler of claim 2, wherein the second connector includes a pin disposed between the mating portion and the connecting portion, and the pin at least partially extends into the first valve when the first connector is coupled to the collar and the collar is coupled to second connector.

19. A coupler comprising:

a first connector having a first end, a second end opposite the first end, a central axis extending through at least the first end and the second end, a body disposed between the first end and the second end, and a first valve disposed proximate the second end, the body having an interior space housing the first valve and a biasing element coupled to the first valve;

a second connector having a threaded mating portion, a connecting portion opposite the mating portion, a second valve disposed within the mating portion, and a pin disposed at least partially within the mating portion; and a collar having a releasing portion detachably coupled to the first connector and a body threadably coupled to the mating portion of the second connector, the releasing portion having a slot that opens and longitudinally extends through the releasing portion and receives at least a portion of the first connector when the releasing portion is coupled to the first connector, wherein the collar is configured to couple the first connector to the second connector such that at least the second end of the first connector is disposed within the second connector, wherein the first connector is configured to decouple from the collar and the second connector in response to a pullout force exceeding a predetermined threshold force, wherein the slot is configured to close when the first connector decouples from the collar, wherein the first connector is prevented from re-coupling to the second connector and the collar when the slot is closed, wherein the central axis extends through the first connector, the collar, and the second connector when the collar is coupled to the first connector and the second connector.

* * * * *